(12) United States Patent
Fischer et al.

(10) Patent No.: US 7,049,271 B2
(45) Date of Patent: May 23, 2006

(54) PHENYL-SUBSTITUTED 2-ENAMINO-KETONITRILES

(75) Inventors: Reiner Fischer, Monheim (DE); Jutta Böhmer, Köln (DE); Ralf Wischnat, Köln (DE); Mark Wilhelm Drewes, Langenfeld (DE); Peter Dahmen, Neuss (DE); Rolf Pontzen, Leichlingen (DE); Peter Lösel, Leverkusen (DE); Christoph Erdelen, Leichlingen (DE); Dieter Feucht, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/275,525

(22) PCT Filed: Apr. 25, 2001

(86) PCT No.: PCT/EP01/04636

§ 371 (c)(1),
(2), (4) Date: Nov. 5, 2002

(87) PCT Pub. No.: WO01/85673

PCT Pub. Date: Nov. 15, 2001

(65) Prior Publication Data

US 2003/0220196 A1   Nov. 27, 2003

(30) Foreign Application Priority Data

May 8, 2000  (DE)  ................................ 100 21 900

(51) Int. Cl.
*C07C 327/00* (2006.01)
*C07C 233/00* (2006.01)
*A01N 37/00* (2006.01)
*A01N 37/34* (2006.01)

(52) U.S. Cl. ..................... 504/307; 504/309; 504/330; 504/239; 504/251; 504/260; 564/78; 564/161; 564/163; 564/164; 564/168; 564/169; 564/180; 564/182; 544/335; 544/322; 546/268.1; 546/269.7; 546/271.4; 546/270.1; 548/190; 549/69

(58) Field of Classification Search ................. 564/78, 564/161, 163, 164, 168, 169, 180, 182; 544/322, 544/335; 546/268.1, 269.7, 271.4, 270.1; 548/190; 549/69; 504/239, 251, 260, 307, 504/309, 330, 266, 268
See application file for complete search history.

(56) References Cited

U.S. PATENT DOCUMENTS

| 2,734,912 | A |   | 2/1956  | Leibu et al. ................. 260/475 |
| 3,865,863 | A |   | 2/1975  | Field et al. ................. 260/465 E |
| 4,173,650 | A | * | 11/1979 | Hanifin et al. ................. 514/520 |
| 4,181,677 | A | * | 1/1980  | Hanifin et al. ................. 558/405 |
| 4,680,401 | A |   | 7/1987  | Grohe ........................ 546/153 |
| 4,686,221 | A | * | 8/1987  | Uno et al. ............. 514/253.08 |
| 4,699,992 | A |   | 10/1987 | Grohe ........................ 558/405 |
| 4,782,156 | A |   | 11/1988 | Grohe ........................ 546/153 |
| 4,914,228 | A |   | 4/1990  | Grohe ........................ 560/103 |
| 4,990,646 | A |   | 2/1991  | Grohe ........................ 558/405 |
| 6,455,472 | B1|   | 9/2002  | Fischer et al. ............. 504/138 |
| 2003/0130125 | A1 |   | 7/2003 | Fischer et al. ............. 504/283 |

FOREIGN PATENT DOCUMENTS

| CA | 2 394 002 | 6/2001 |
| DE | 100 07 286 | 8/2001 |
| EP | 2 808 070 | 8/1979 |
| EP | 0 168 737 | 1/1986 |
| EP | 0 220 523 | 5/1987 |
| EP | 0 348 002 | 12/1989 |
| EP | 0490220 | 12/1991 |
| EP | 0 290 220 | 6/1992 |
| JP | 63-132881 | 6/1988 |
| JP | 2-286668 | 11/1990 |
| JP | 10 175937 | * 6/1998 |
| JP | 10-175937 | 6/1998 |
| WO | 99/11601 | 3/1999 |
| WO | 99/16753 | 4/1999 |

OTHER PUBLICATIONS

Definitions of "noble metal" from Enyclopedia Britanninca; natiomaster.com; Eric Weisstein World of Chemistry; and The american Heritage Dict. English Language: Fourth Edition, 2000.*
** Database Crossfire Beilstein 'Online! Beilstein Institut zur Förderung der Chemischen Wissenschaften, Frankfurt am Main, DE; Data base accession No. BRN 7429725 XP002179949 abstract & Bagdanowicz-Szwed et al.: Monatsh. Chem., vol. 126, No. 12, 1995, pp. 1341-1348, cited in the application.

(Continued)

*Primary Examiner*—James O. Wilson
*Assistant Examiner*—Kahsay Habte
(74) *Attorney, Agent, or Firm*—Richard E. L. Henderson; Raymond J. Harmuth

(57) ABSTRACT

The present invention relates to novel phenyl-substituted 2-enamino-ketonitriles of the formula (I):

(I)

in which
Ar, X, Z, Y and K are each as defined in the description, to a plurality of processes for their preparation and to their use as herbicides and pesticides.

5 Claims, No Drawings

OTHER PUBLICATIONS

** Chemical Abstracts, vol. 131, No. 5, Aug. 2, 1999, Columbus, Ohio, US; abstract No. 58717, Ostrowska, Katarzyna et al: "Synthesis and transamination of enaminones. Derivatives of 1-phenyl-4-(phenylhydroxymethylidene)pyrrolidine-2, 3, 5-trione" XP002179935 RN227766-04-3 & Monatsh. Chem. (1999), 130(4), 555-562, 1999.

** Chemical Abstracts, vol. 129, No. 3, Jul. 20, 1998 Columbus, Ohio, US; abstract No. 27962, Uchiyama, Hiroko et al: "Preparation of quinolonecarboxylic acid derivatives and analogs as TNF production inhibitors" XP002179936 RN 153469-01-3 & JP 10 130149 A (Sankyo Co., Ltd., Japan; UBE Industries, Ltd.) May 19, 1998.

** Chemical Abstracts, vol. 125, No. 19, Nov. 4, 1996, Columbus, Ohio, US; abstract No. 247745, Sherif, Sherif M. et al: ".beta.-Enaminonitriles in heterocyclic synthesis: a novel one-pot synthesis of thiophenes and their fused derivatives" XP002179937 , RN 182056-29-7 & J. Chem. Res., Synop. (1996), (8), 356-357, 1996.

** Chemical Abstracts, vol. 112, No. 21, May 21, 1990 Columbus, OH, US; abstract No. 198272, Ibrahim, Nadia Sobhy et al: "Nitriles in organic synthesis of new pyridazine, pyridine and pyrazolo '3, 4-b]pyridine derivatives" XP002179938 RN 126679-95-6, 126679-94-5, 126679-93-4, 126679-91-2 & J. Prakt. Chem. (1989), 331(3), 375-9, 1989.

** Chemical Abstracts, vol. 112, No. 6, Feb. 5, 1990 Columbus, Ohio, US; abstract No. 47532, Basato, Marino et al: "Metal-catalyzed addition of fluorinated.beta.-oxo amides to cyanogen: synthesis and characterization of the products and of related catalytic copper(II) intermediates" XP002179939 RN 124637-44-1 & Gazz. Chim. Ital. (1989), 199(6), 339-43, 1989.

**Chemical Abstracts, vol. 110, No. 11, Mar. 13, 1989 Columbus, Ohio, US; abstract No. 95088, Ibrahim, Nadia S. et al: "Nitriles in organic synthesis. A route to polyfunctionally substituted azabiaryls" XP002179940 RN 118128-91-9, 118128-90-8, 118128-89-5 & Arch. Pharm. (Weinheim, Ger.) (1988), 321(9), 569-70, 1988.

**Chemical Abstracts, vol. 106, No. 23, Jun. 8, 1987 Columbus, Ohio, US; abstract No. 195846, Alberola, A. et al: "Ring cleavage of N-alkylisoxazolium salts by lithium dialkylcuprates. Synthesis of .beta.-enamino ketones" XP002179941 RN 108086-96-0 & Synth. Commun. (1986), 16(6), 673-80, 1986.

**Chemical Abstracts, vol. 97, No. 5, Aug. 2, 1982 Columbus, Ohio, US; abstract No. 38879, Grohe, Klaus et al: "Enehydrazines. I. Acylation of tautomerizable enehydrazines" XP002179942 RN 82275-56-7 & Liebigs Ann. Chem. (1982), (5), 884-93, 1982.

**Database Crossfire Beilstein 'Online! Beilstein Institut zur Förderung der Chemischen Wissenschaften, Frankfurt am Main, DE; Data base accession No. BRN 4811766 XP002179944, abstract & Donati et al: Gazz. Chim Ital., vol. 121, No. 7, 1991, pp. 329-334.

**Database Crossfire Beilstein 'Online! Beilstein Institut zur Förderung der Cheischen Wissenschaften, Frankfurt am Main, DE; Database accession No. BRN 2640580 XP002179945 abstract & Huffman: J. Org. Chem., vol. 27, 1962, pp. 551-558.

**Database Crossfire Beilstein 'Online! Beilstein Institut zur Förderung der Chemischen Wissenschaften, Frankfurt am Main, DE; Database accession No. BRN 2657818 XP002179946 abstract & Coenen et al.; J. Prakt. Chem., vol. 27, 1965, pp. 239-250.

**Database Crossfire Beilstein 'Online! Beilstein Institut zur Förderung der Chemischen Wissenschaften, Frankfurt am Main, DE; Database accession No. BRN 3531635, 5576979 XP002179947 cited in the application abstract & Sarkar et al.: Indian J. Chem., Sect. B, vol. 25, 1986, pp. 1133-1137.

**Database Crossfire Beilstein 'Online! Beilstein Institut zur Förderung der Chemischen Wissenschaften, Frankfurt am Main, DE; Database accession No. BRN 3532739 XP002179948 abstract & Burns: J. Prakt. Chem., vol. 2, No. 47, 1893, p. 112.

**Database Crossfire Beilstein 'Online! Beilstein Institut zur Förderung der Chemischen Wissenschaften, Frankfurt am Main, DE; Database accession No. BRN 3343703 XP002179943 abstract & Benary et al.: Chem. Ber., vol. 59, 1926, p. 2548.

Indian Journal of Chemistry, vol. 25B, Nov. 1986, pp. 1113-1137, "Studies on β- Enaminonitriles: Part I—Benzoylation in Presence of Sodium in Benzene" by M. Sarkar et al.

J. Med. Chem. (month unavailable) 1990, 33, pp. 380-386, "6-Benzoxazinylpyridazin-3-ones: Potent, Long-Acting Positive Inotrope and Peripheral Vasodilator Agents" by D. W. Combs et al.

Can J. Chem., 61, Apr. 1983, pp. 2581-2589, "Reaction entre solvant et espèces intermédiares' apparues lors de l'électroréduction—acylation de la fluorénone et de la fluorènone-anil dans l'acétonitrile" by C. Degrand et al.

Journal of Organometallic Chemistry, 482, (month unavailable) 1994, pp. 45-51, "Carbonylation of bromobenzene in a biphasic medium catalysed by water-soluble palladium complexes derived from tris(3-sulphophenyl)phosphine" by F. Monteil et al.

Nouv. J. Chim., vol. 1, (month unavailable) 1977, pp. 235-241, "New Evidence Of Stereoelectronic Control From The Basic Hydrolysis Of Esters, Lactones, Amides and Lactams. Carbonyl Oxygen Exchange. Reversible Ring Opening Of Lactams And Lactones" by P. Deslongchamps et al.

Helvetic Chimica Acta—vol. 54, fasc. 2, Jan. 1971, Nr. 69-70, pp. 710-734, "70. Sulfidknontracktion viaalkylativ Kupplung: eine Methode zur Darstellung von β-Dicarbonylderivaten Über synthetische Methoden. 1. Mitteilung" by von M. Roth et al.

Journal of Molecular Catalysis A: Chemical 154, Oct. 1999, pp. 93-101, "Carbonylation of benzyl bromide to benzeneacetic acid and its esters catalysed by water-soluble palladium complexes" by A. M. Trzeciak et al.

J. Heterocyl. Chem., Sep. 15, 1979, pp. 1109-1111, "Pyrimidine Derivatives and Related Compounds. A Novel Synthesis of Pyrimidines, Pyrazolo[4, 3-d]pyrimidine." M. Hilmy Elnagdi et al.

Arch. Pharm. (Weinheim) 320, 487-491, (month unavailable) 1987, pp. 487-491, "Synthesis of New 3-(Pyridin-6-yl)pyrazolo[1,5-a]pyrimidenes" by N. Sobhy Ibrahim et al.

Chem. Ber., Jan. 1965, pp. 2754-2761, Umsetzungen von N-Monoalkyl-form- und-acetamiden mit Dimethylsulfat—Synthesen von N-Monoalkylimidsäureestern and symmetrischen N.N'-Dialkyl-Formamidinen[2] by H. Bredereck et al.

Pharmazie, 51, (month unavailable) 1996, pp. 805-810, "Pyrrolidino enaminones structural related to gyrase inhibitors: synthesis, cyclization and pharmacological activity" by G. Dannhardt et al.

Tetrahedron 54, (month unavailable) 1998, pp. 15861-15869, "An Asymmetric Synthesis of L-[3-$^{13}$C]Tyrosine from [$^{13}$C]Carbon Monoxide" by K. Takatori et al.

Monatshefte für Chemie 109, pp. 527-535, (month unavailable) 1978, "Zur Synthesen von 4-Aminochinolinen durch intramolekular *Friedel—Crafts*-Reaktion" by H. Schäfer et al.

J. Am. Chem., Oct. 21, 1970, pp. 6360-6362, "Barrier to Inversion at Nitrogen in Imines, Configurational Studies on *O*-Methyl Imidates" by R. M. Moriarty et al.

J. Chem. Soc., Perkin Trans. I, (month unavailable) 1985, pp. 1499-1501, "Activated Nitriles in Heterocyclic Synthesis: Reaction of Cyanogen Bromide with some Functionally Substituted Enamines" by Z. El-Shahat Kandeel et al.

J. Chem. Soc. Perkin Trans. 1, (month unavailable) 1979, pp. 2481-2487, "The Oxidation of Trimethylsilylated Amides to Hydroxamic Acids" by S. A. Matlin et al.

J. Chem. Soc., (month unavailable) 1951, pp. 2758-2760, "Experiments on the Synthesis of Carbonyl Compounds. Part V. β-Keto-esters and -Nitriles." by R. E. Bowman et al.

J. Indian Chem. Soc., vol. 48, No. 10, (month unavailable) 1971, pp. 953-956, "Thiopegan Derivatives. Part XLIX" by H. K. Gakhar et al.

Collection Czechoslovak Chem. Commun. [vol. 51], (month unavailable) 1986, pp. 2193-2198, "Synthesis of Some New Pyrazolo[1,5-a]Pyrimidine and Pyrazolo[1,5-*c]-as*-Triazine Derivatives" by A. Ghani A.Elagamey et al.

Chem. Ind. (London), 17, Sep. 5, 1988, pp.: 563-564, "Activated nitriles in heterocyclic synthesis of thiazinone, quinazolinone and benzimidazole derivatives" by N. Sobhy Ibrahim et al.

Tetrahedron, vol. 52, No. 31, pp. 10389-10398, (month unavailable) 1996, "Double Diastereoselective Glucosidation of Cyclic Hemiacetals: Synthesis of the 1, 4-Benzoxazinone Acetal Glucosides GDIBOA and GDIMBOA from *Gramineae*" by M. Kluge et al.

C. R. Acad. Sci Paris, t. 321, Sérle II b, pp. 521-524, (month unavailable) 1995, "Réactions d'annélation stéréosélectives au deépart d'une β-énaminone cyclique: l'α-pyrrolidinylidène-acétophénone" by V. Issartel et al.

Organikum, 16th revised edition, pp. 415-499, (month unavailable) 1986, "D. 7.1.4.3. Hydrolyse von Carbonsäurederivaten".

Heteroxyxles, vol. 23, No. 10, (month unavailable) 1985, pp. 2645-2649, "A Convenient Synthesis of 2-Alkyl- and 2-Arylamino-4-Aryl-5-CYA Nothiazoles" by A. Corsaro et al.

Angew Chem. 23, (English Translation), (month unavailable) 1984, pp. 732-734, "Metal-Catalyzed Carbonylations of Benzyl and Aryl Bromides in the Presence of Aluminum Alkoxides: A Straightforward Ester Synthesis" by H. Alper et al.

Synthesis, 9, (month unavailable) 1982, pp. 791-792, "Synthesen mit Nitrilen; 63$^1$. 3-Benzoylpyrido[1,2-]pyrimidin-4-one" by H. Junek et al.

Khim-Farm. Zh., 24,(7), (month unavailable) 1990, pp. 24-27, R. G. Glushkov et al, See Translation Attached.

Khim-Fram. Zh., (month unavailable) 1991, pp. 19-23, M. V. Mezentseva et al, See Translation Attached.

* cited by examiner

PHENYL-SUBSTITUTED 2-ENAMINO-KETONITRILES

The invention relates to novel phenyl-substituted 2-enamino-ketonitriles, to a plurality of processes for their preparation and to their use as crop protection agents, in particular as herbicides, acaricides, nematicides and insecticides Certain 2-enamino-ketonitriles which are substituted on the phenyl ring and have herbicidal action have already been disclosed, for example in EP-A 0 348 002. However, these 2-[3-phenoxy- or 3-[(2-pyridyloxy)benzoyl]-3-(dialkylamino)acrylonitriles have hitherto not attained any importance.

Likewise without any significant importance are the compounds with herbicidal properties disclosed in JP-A2 10 175 937, WO 99/16753 and EP-A 0 490 220.

Furthermore, 2-enamino-ketonitriles have been disclosed for use as intermediates for the synthesis of antibacterial active compounds, see DE-A 35 02 935, EP-A 0 220 523, DE 34 26 483 and EP-A 0 168 737.

Further 2-enamino-ketonitriles are also known from DE-A 19 958 164, DE-A 19 851 986, DE-A 10 007 286 and WO 00/27812.

Also known are 2-enamino-ketonitriles which are unsubstituted on the phenyl ring (I. N. Sobhy, H. S. Zahi, M. M. Hassan, E. M. Hilmy, (Chem. Ind. (London), 1988, 17, 563–564), I. N. Sobhy, M. M. Hassan, E. M. Hilmy (Arch. Pharm. 1987, 320 (6), 487–491), E. A. Ghani, M. A. Fathy, F. A. Amer, Collet. Czech, Chem. Commun. (1986, 51, 2193–2198), C. Degrand, G. Belot, P-L. Compagnon, F. Jasquez, Can. J. Chem. (1983, 61, 2581–2589), E. M. Hilmy, M. S. Fahmy, E. A. A. Hafez, R. M. Elmoghayar J. Heterocyl. Chem. (1979, 16, 1109–1111), H. Schäfer, K. Gewald, Monatsh. Chem. (1978), 109, 527–535). M. Savkar, S. Chattopadhyay, K. K. Mahalanabis, Ind. J. Chem. Sect. B (1996, 25 B, 1133–1137). Z. E. S. Kandeel, F. M. Abelrazeh, M. E. Eldin, J. Chem. Soc. Perk. Trans. 1 (1985, 7, 1499–1501), H. Jurek, H. W. Schmidt, G. Gfrerer, Synthesis, (1982, 9, 791) K. Gewald, H. Schäfer, K. Sattler, Monatsh. Chem. (1979, 110, 1189).

However, a use of these compounds as crop protection agents has hitherto not been described.

The formula (I) provides a general definition of the novel 2-enamino-ketonitriles

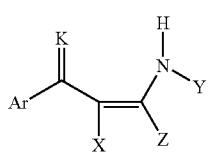

(I)

in which
K represents oxygen or sulphur,
Ar represents in each case optionally substituted phenyl, naphthyl, represents in each case optionally substituted mono- or bicyclic hetaryl having 5 to 10 ring atoms, or represents the group

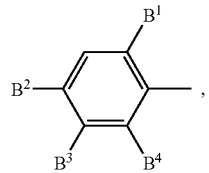

where
$B^1$ represents hydrogen or halogen,
two adjacent radicals—$B^2$ and $B^3$ or $B^3$ and $B^4$—together represent one of the groupings below
-$Q^1$-$CQ^2$-, -$Q^1$-$CQ^2$-$Q^3$-, -$Q^1$-$C(B^6,B^7)$-$Q^3$-, —$C(B^6,B^7)$—$CQ^2$-, —$C(B^6,B^7)$-$Q^1$-$CQ^2$-, -$Q^1$-$C(B^6,B^7)$—$C(B^6,B^7)$—, -$Q^1$-$C(B^6,B^7)$—$C(B^6,B^7)$-$Q^3$-, —$C(B^6,B^7)$—$C(B^6,B^7)$—$CQ^2$-, -$Q^1C(B^6)$=$C(B^6)$—, —$C(B^6)$=$C(B^6)$—$CQ^2$-, -$Q^1$-$C(B^6,B^7)$—$CQ^2$-, —$N(B^8)$—$C(B^6,B^7)$—$CQ^2$-, —$C(B^6)$=N—, -$Q^1$-$CQ^2$-$C(B^6,B^7)$—, -$Q^1$-$CQ^2$-$N(B^8)$—, -$Q^1$-$C(B^6,B^7)$—$CQ^2$-$N(B^8)$—, —$C(B^6,B^7)$-$Q^1$-$CQ^2$-$N(B^8)$—, —$C(B^6,B^7)$—$C(B^6,B^7)$—$N(B^8)$—, —$C(B^6,B^7)$—$C(B^6,B^7)$—$CQ^2$-N$(B^8)$—, —$C(B^6)$=$C(B^6)$—$N(B^8)$—, —$C(B^6)$=$C(B^6)$—$CQ^2$-$N(B^8)$—, —$C(B^6,B^7)$—$CQ^2$-$N(B^8)$, —$N(B^8)$—$C(B^6,B^7)$—$CQ^2$-$N(B^8)$—, —$C(B^6)$=N—N$(B^8)$—, -$Q^1$-$CQ^2$-$C(B^6,B^7)$—$N(B^8)$—, -$Q^1$-$C(B^6,B^7)$—$C(B^6,B^7)$—$CQ^2$-$N(B^8)$—, —$N(B^8)$—$CQ^2$-$C(B^6)$=N—, -$Q^1$-$C(B^6)$=$C(B^6)$-$Q^3$-, —$N(B^8)$—$C(B^6)$=$C(B^6)$—$CQ^2$-, —$N(B^8)$—$C(B^6)$=N—, —$N(B^8)$—$C(B^6,B^7)$—$C(B^6,B^7)$-$Q^3$-, —$N(B^8)$—$CQ^2$-$C(B^6,B^7)$-$Q^4$-, —$N(B^8)$—$CQ^2$-$CQ^2$-$Q^3$-, -$Q^1$-$C(B^6)$=$C(B^6)$—$C(B^6,B^7)$—, -$Q^1$-$C(B^6)$=$C(B^6)$—, and the fourth radical, $B^4$ or $B^2$, represents hydrogen, thiocarbamoyl, cyano or halogen,
where
$Q^1$, $Q^2$ and $Q^3$ are identical or different and each represent oxygen or sulphur, and
$Q^4$ represents —SO— or —SO$_2$—,
$B^6$ and $B^7$ are identical or different and individually represent hydrogen, halogen or alkyl or together represent alkanediyl, and
$B^8$ represents hydrogen, hydroxyl, represents in each case optionally cyano-, halogen-, alkoxy-, alkylcarbonyl- or alkoxycarbonyl-substituted alkyl, alkylcarbonyl, alkoxycarbonyl, alkylthio or alkylsulphonyl, represents in each case optionally halogen-substituted alkenyl or alkinyl, represents in each case optionally halogen- or alkyl-substituted cycloalkyl or cycloalkylalkyl, represents in each case optionally halogen-substituted alkoxy or alkenyloxy, represents in each case optionally cyano-, halogen-, alkyl-, halogenoalkyl-, alkoxy- or halogenoalkoxy-substituted arylalkyl or arylalkoxy,
X represents CN,

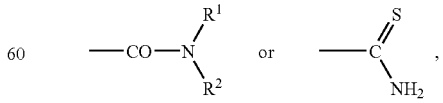

Y represents hydrogen, represents in each case optionally substituted alkyl, alkenyl, alkinyl, alkoxyalkyl, alkylthioalkyl, represents in each case optionally substituted cycloalkyl or cycloalkylalkyl which are in each case optionally interrupted in the cycle by heteroatoms, or represents in each case optionally substituted phenylalkyl or hetarylalkyl, Z represents hydrogen, represents in each case optionally substituted alkyl, phenyl or phenylalkyl, $R^1$ represents hydrogen, represents in each case optionally substituted saturated or unsaturated alkyl or cycloalkyl, each of which is optionally interrupted by heteroatoms, represents in each case optionally substituted phenyl or hetaryl, represents in each case optionally substituted phenylalkyl or hetarylalkyl, and $R^2$ represents hydrogen, represents in each case optionally substituted saturated or unsaturated alkyl or alkoxy, represents in each case optionally substituted phenyl, phenylalkyl or phenylalkyloxy, or $R^1$, $R^2$ furthermore together with the nitrogen atom to which they are attached represent an optionally substituted cycle which is optionally substituted by a plurality of heteroatoms.

For the compounds of the formula (I), the following applies:

Ar preferably represents $Ar^1$, where $Ar^1$ represents phenyl, naphthyl or mono- or bicyclic hetaryl having five to ten ring atoms, each of which radicals is optionally mono- to pentasubstituted by halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulphonyl, $C_1$–$C_6$-halogenoalkyl, $C_1$–$C_6$-halogenoalkoxy, $C_2$–$C_8$-halogenoalkenyloxy, $C_1$–$C_2$-alkylidenediyl-dioxy, $C_1$–$C_2$-halogenoalkylidenediyl-dioxy, halogeno-$C_1$–$C_4$-alkylthio, halogeno-$C_1$–$C_4$-alkylsulphonyl, phenyl-$C_1$–$C_4$-alkoxy, hydroxyl, mercapto, nitro, cyano, amino or by the groups a)

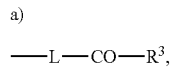
—L—CO—$R^3$, b)

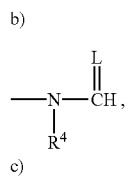

c)

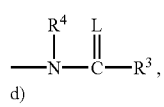

d)

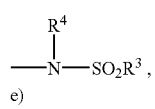

e)

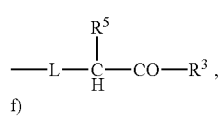

f)

or represents $Ar^2$, where $Ar^2$ represents $Ar^1$ which is additionally substituted by phenyl, naphthyl, five- or six-membered hetaryl, phenyl-$C_1$–$C_4$-alkyl, phenoxy, phenyl-S(O)$_g$—, five- or six-membered hetaryloxy or hetaryl-S(O)$_g$, where these substituents for their part are in each case optionally mono- to tetrasubstituted by halogen, $C_1$–$C_6$-alkyl, $C_1$–$C_6$-alkenyl, $C_1$–$C_6$-alkoxy, $C_1$–$C_4$-halogenoalkyl, $C_1$–$C_4$-halogenoalkoxy, nitro or cyano, where g represents 0, 1 or 2, or represents the group

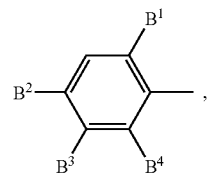

where $B^1$ represents hydrogen or halogen, two adjacent radicals—$B^2$ and $B^3$ or $B^3$ and $B^4$—together represent one of the groupings below -$Q^1$-$CQ^2$-N($B^8$)—, -$Q^1$-C($B^6$,$B^7$)—$CQ^2$-N($B^8$)—, —N($B^8$)—C($B^6$,$B^7$)-$CQ^2$-N($B^8$)—, -$Q^1$-$CQ^2$-C($B^6$,$B^7$)—N($B^8$)—, -$Q^1$-C($B^6$)=C($B^6$)—C($B^6$,$B^7$)—, -$Q^1$-C($B^6$)=C($B^6$)—, —N($B^8$)—$CQ^2$-C($B^6$)=N— where $Q^1$ and $Q^2$ are identical or different and each represent oxygen or sulphur, $B^6$ and $B^7$ are identical or different and individually represent hydrogen or methyl, $B^8$ represents hydrogen, hydroxyl, represents in each case optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents in each case optionally fluorine-, chlorine- or bromine-substituted propenyl, butenyl, propinyl or butinyl, represents in each case optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl, cyclohexylmethyl, represents in each case optionally fluorine- and/or chlorine-substituted methoxy, ethoxy, n- or i-propoxy, n-, i- or s-butoxy, propenyloxy or butenyloxy, or represents in each case optionally cyano-, fluorine-, chlorine-, methyl-, ethyl-, trifluoromethyl-, methoxy-, ethoxy-, difluoromethoxy- or trifluoromethoxy-substituted benzyl or benzyloxy, and the fourth radical, $B^4$ or $B^2$, represents hydrogen, cyano, fluorine or chlorine, K preferably represents oxygen or sulphur.

L preferably represents oxygen or sulphur.

X preferably represents CN,

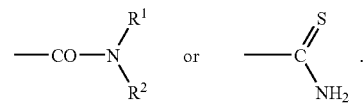

Y preferably represents hydrogen, in each case optionally mono- or polyhydroxy-substituted $C_1$–$C_{12}$-alkyl, $C_3$–$C_{10}$-alkenyl, $C_3$–$C_{10}$-alkinyl, $C_1$–$C_6$-alkoxy-$C_2$–$C_4$-alkyl, di-$C_1$–$C_6$-alkoxy-$C_2$–$C_4$-alkyl, $C_1$–$C_6$-alkoxy-$C_2$–$C_4$-cyanoalkyl, $C_1$–$C_6$-alkylthio-$C_2$–$C_4$-alkyl, $C_1$–$C_8$-halogenoalkyl, $C_1$–$C_8$-halogenoalkenyl or $C_1$–$C_8$-cyanoalkyl, represents in each case optionally $C_1$–$C_6$-alkyl-, $C_1$–$C_6$-alkoxy-, $C_1$–$C_4$-halogenoalkyl-, cyano-, halogenophenyl-, benzyl-, $C_1$–$C_6$-hydroxyalkyl- or halogen-substituted $C_3$–$C_8$-cycloalkyl or $C_3$–$C_8$-cycloalkyl-$C_1$–$C_4$-alkyl which are optionally interrupted in the cycle by oxygen, sulphur or nitrogen, represents phenyl-$C_1$–$C_4$-alkyl or five- or six-membered hetaryl-$C_1$–$C_4$-alkyl, each of which is optionally mono- to tetra-substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents hydrogen, $C_1$–$C_6$-alkyl, represents phenyl or phenyl-$C_1$–$C_4$-alkyl, each of which is optionally mono- to trisubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^1$ preferably represents hydrogen, represents in each case optionally fluorine- and/or chlorine-substituted $C_1$–$C_{10}$-alkyl, $C_3$–$C_{10}$-alkenyl, $C_3$–$C_6$-alkinyl, represents in each case optionally fluorine-, chlorine-, $C_1$–$C_4$-alkyl-, $C_1$–$C_4$-alkoxy-substituted $C_3$–$C_8$-cycloalkyl or $C_5$–$C_8$-cycloalkenyl in which optionally one methylene group may be replaced by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^2$ preferably represents hydrogen, $C_1$–$C_6$-alkyl or $C_3$–$C_6$-alkenyl.

$R^1$, $R^2$ preferably furthermore together with the nitrogen atom to which they are attached represent an in each case optionally $C_1$–$C_4$-alkyl-substituted five- to eight-membered cycle in which optionally one methylene group may be replaced by oxygen or sulphur.

$R^3$ preferably represents in each case optionally fluorine- and/or chlorine-substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case optionally fluorine-, chlorine-, $C_1$–$C_4$-alkyl-, $C_1$–$C_4$-alkoxy-substituted $C_3$–$C_8$-cycloalkyl or $C_3$–$C_8$-cycloalkoxy in which optionally one methylene group may be replaced by oxygen or sulphur, represents phenyl, phenoxy, benzyloxy, five- or six-membered hetaryl or phenyl-$C_1$–$C_4$-alkyl, each of which may optionally be mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or, in the case of the radicals a), c) and f) mentioned under Ar, also represents a group

$R^4$ preferably represents hydrogen or $C_1$–$C_4$-alkyl.

$R^5$ preferably represents hydrogen or optionally fluorine- and/or chlorine-substituted $C_1$–$C_4$-alkyl.

$R^6$ preferably represents hydrogen, in each case optionally fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, optionally fluorine-, chlorine-, $C_1$–$C_4$-alkyl- or $C_1$–$C_4$-alkoxy-substituted $C_3$–$C_8$-cycloalkyl in which optionally one methylene group may be replaced by oxygen or sulphur, represents phenyl, phenyl-$C_1$–$C_4$-alkyl or phenyl-$C_1$–$C_2$-alkoxy, each of which may optionally be mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^7$ preferably represents hydrogen, $C_1$–$C_6$-alkyl or $C_3$–$C_6$-alkenyl.

$R^6$, $R^7$ preferably furthermore together with the nitrogen atom to which they are attached represent an optionally $C_1$–$C_4$-alkyl-substituted five- to eight-membered cycle in which optionally one methylene group may be replaced by oxygen or sulphur.

K particularly preferably represents oxygen or sulphur.

Ar particularly preferably represents $Ar^1$, where $Ar^1$ represents phenyl, naphthyl, quinolinyl, thienyl, pyrimidyl, furanyl, thiazolyl, benzothiazolyl, oxazolyl, pyrazolyl or pyridyl, each of which is optionally mono- to trisubstituted by fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, $C_1$–$C_2$-alkylidenediyl-dioxy, $C_1$–$C_2$-halogenoalkylidenediyl-dioxy, halogeno-$C_1$–$C_2$-alkylthio, halogeno-$C_1$–$C_2$-alkylsulphonyl, phenyl-$C_1$–$C_4$-alkoxy, hydroxyl, mercapto, nitro, cyano, amino or by one of the groups below a)

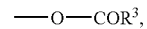

b)

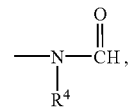

c)

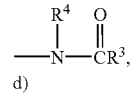

d)

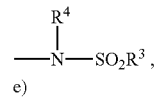

e)

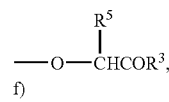

f)

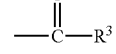

or represents $Ar^2$, where $Ar^2$ represents $Ar^1$ which is additionally substituted by phenyl, pyridyl, pyrimidyl, thienyl, furanyl, thiazolyl, tetrazolyl, triazolyl, benzyl, phenoxy, phenyl-S(O)$_g$—, pyridyloxy, pyrimidyloxy, thiazolyloxy, pyridyl-S(O)$_g$—, pyrimidyl-S(O)$_g$— or thiazolyl-S(O)$_g$—, where these substituents for their part are optionally mono- to trisubstituted by fluorine, chlorine, bromine, $C_1$–$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano, where g represents 0, 1 or 2, or represents the group

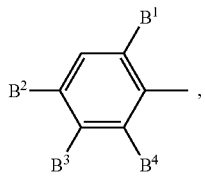

where
B¹ represents hydrogen or halogen,
two adjacent radicals—B² and B³ or B³ and B⁴—together represent the grouping below

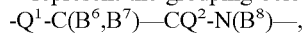

-Q¹-C(B⁶,B⁷)═CQ²-N(B⁸)—, where
$Q^1$ and $Q^2$ are identical or different and each represents oxygen or sulphur,
$B^6$ and $B^7$ are identical or different and individually represent hydrogen or methyl,
$B^8$ represents hydrogen, hydroxyl, represents in each case optionally cyano-, fluorine-, chlorine-, methoxy-, ethoxy-, acetyl-, propionyl-, methoxycarbonyl- or ethoxycarbonyl-substituted methyl, ethyl, n- or i-propyl, n-, i-, s- or t-butyl, represents in each case optionally fluorine-, chlorine- or bromine-substituted propenyl, butenyl, propinyl or butinyl, represents in each case optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl, cyclohexylmethyl, represents in each case optionally fluorine- and/or chlorine-substituted methoxy, ethoxy, n- or i-propoxy, n-, i- or s-butoxy, propenyloxy or butenyloxy, or represents in each case optionally cyano-, fluorine-, chlorine-, methyl, ethyl-, trifluoromethyl-, methoxy-, ethoxy-, difluoromethoxy- or trifluoromethoxy-substituted benzyl or benzyloxy,
and the fourth radical, $B^4$ or $B^2$, represents hydrogen, cyano, fluorine or chlorine,
X particularly preferably represents CN,

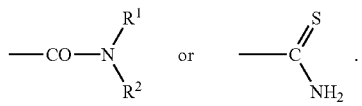

Y particularly preferably represents hydrogen, represents in each case optionally mono- or poly-hydroxy-substituted $C_1$–$C_{10}$-alkyl, $C_1$–$C_6$-halogenoalkyl, $C_3$–$C_8$-alkenyl, $C_3$–$C_8$-alkinyl, $C_1$–$C_4$-alkoxy-$C_2$–$C_3$-alkyl, di-$C_1$–$C_4$-alkoxy-$C_2$–$C_4$-alkyl, $C_1$–$C_4$-alkoxy-$C_2$–$C_4$-cyanoalkyl, $C_1$–$C_4$-alkylthio-$C_2$–$C_3$-alkyl, $C_1$–$C_6$-halogenoalkenyl or $C_1$–$C_6$-cyanoalkyl, represents in each case optionally $C_1$–$C_4$-alkyl-, $C_1$–$C_4$-alkoxy-, $C_1$–$C_2$-halogenoalkyl-, cyano-, halogenophenyl-, benzyl-, $C_1$–$C_4$-hydroxyalkyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or nitrogen, represents phenyl-$C_1$–$C_3$-alkyl, thiazolylmethyl, triazolylmethyl or pyridylmethyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents hydrogen, $C_1$–$C_3$-alkyl, represents phenyl or benzyl, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.
$R^1$ particularly preferably represents hydrogen, represents in each case optionally fluorine and/or chlorine-substituted $C_1$–$C_6$-alkyl, $C_2$–$C_6$-alkenyl, $C_3$–$C_4$-alkinyl, represents optionally fluorine-, chlorine-, $C_1$–$C_2$-alkyl-, $C_1$–$C_2$-alkoxy-substituted $C_3$–$C_6$-cycloalkyl or represents phenyl or benzyl, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.
$R^2$ particularly preferably represents hydrogen, represents $C_1$–$C_4$-alkyl or $C_3$–$C_4$-alkenyl, each of which is optionally substituted by fluorine and/or chlorine.
$R^1$, $R^2$ particularly preferably furthermore together with the nitrogen atom to which they are attached represent an optionally methyl-substituted five- or six-membered cycle in which optionally one methylene group may be replaced by oxygen,
$R^3$ particularly preferably represents in each case optionally fluorine- and/or chlorine-substituted $C_1$–$C_6$-alkyl, $C_2$–$C_6$-alkenyl, $C_3$–$C_6$-alkinyl, $C_1$–$C_6$-alkoxy, $C_1$–$C_4$-alkoxy-$C_1$–$C_2$-alkyl, $C_1$–$C_4$-alkylthio-$C_1$–$C_2$-alkyl, in each case optionally fluorine-, chlorine-, $C_1$–$C_2$-alkyl- and/or $C_1$–$C_2$-alkoxy-substituted $C_3$–$C_6$-cycloalkyl or $C_3$–$C_6$-cycloalkoxy in which optionally one methylene group may be replaced by oxygen, represents phenyl, phenoxy, benzyloxy, thienyl, furanyl, pyridyl, pyrimidyl, thiazolyl, pyrazolyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, or, in the case of the radicals a), c) and f) mentioned under Ar, also represents a group

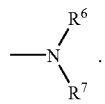

$R^4$ particularly preferably represents hydrogen.
$R^5$ particularly preferably represents hydrogen, methyl or ethyl.
$R^6$ particularly preferably represents hydrogen, in each case optionally fluorine- and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, in which optionally one methylene group may be replaced by oxygen, represents phenyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro.
$R^7$ particularly preferably represents hydrogen or $C_1$–$C_4$-alkyl.
$R^6$, $R^7$ particularly preferably furthermore together with the nitrogen atom to which they are attached represent an optionally $C_1$–$C_2$-alkyl-substituted five- or six-membered cycle in which optionally one methylene group may be replaced by oxygen.
K very particularly preferably represents oxygen and sulphur.

Ar very particularly preferably represents Ar¹, where Ar¹ represents phenyl which is optionally mono- to trisubstituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, benzyloxy, hydroxyl, mercapto, nitro, cyano or amino, or represents pyridyl which is optionally mono- or disubstituted by fluorine, chlorine, bromine, methyl, ethyl, methoxy, ethoxy, propoxy, i-propoxy, butoxy, i-butoxy, methylthio, ethylthio or trifluoromethyl, or represents Ar², where Ar² represents Ar¹ which is additionally substituted by phenyl, pyridyl, thienyl, tetrazolyl, triazolyl or phenoxy, where these substituents are for their part optionally mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, or represents the group

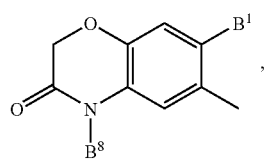

where B¹ represents hydrogen or fluorine and B⁸ represents allyl, propargyl or benzyl, X very particularly preferably represents —CN, —CO—NH₂,

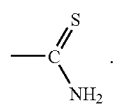

Y very particularly preferably represents hydrogen, in each case optionally mono- or poly-hydroxy-substituted $C_1$–$C_6$-alkyl, $C_1$–$C_4$-halogenoalkyl, $C_3$–$C_6$-alkenyl, $C_3$–$C_6$-alkinyl, $C_1$–$C_4$-alkoxy-$C_2$–$C_3$-alkyl, di-$C_1$–$C_2$-alkoxy-$C_2$–$C_4$-alkyl, $C_1$–$C_2$-alkoxy-$C_2$–$C_4$-cyanoalkyl, $C_1$–$C_2$-alkylthio-$C_2$–$C_3$-alkyl, $C_1$–$C_5$-halogenoalkenyl or $C_1$–$C_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro.

Z very particularly preferably represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro.

R³ very particularly preferably represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, represents phenyl, pyridyl or benzyl, each of which is optionally mono- or disubstituted by fluorine, chlorine, bromine, methyl, n-, s-, i- or t-butyl, methoxy, trifluoromethyl, trifluoromethoxy, cyano or nitro, or in the case of the radicals a), c) and f) mentioned Ar, also represents the group

R⁵ very particularly preferably represents hydrogen or methyl.

R⁶ very particularly preferably represents hydrogen, methyl, ethyl, propyl, isopropyl, n-, s-, i- or t-butyl, cyclopropyl, cyclopentyl, cyclohexyl, represents phenyl which is optionally mono- or disubstituted by fluorine, chlorine, bromine, methyl, methoxy, trifluoromethyl, trifluoromethoxy, cyano or nitro R⁷ very particularly preferably represents hydrogen, methyl or ethyl.

R⁶, R⁷ together with the nitrogen atom to which they are attached very particularly preferably represent a pyrrolidine, piperidine or morpholine radical.

K especially preferably represents oxygen.

Ar especially preferably represents Ar¹, where Ar¹ represents phenyl which is optionally mono- to trisubstituted by fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoro-methylenedioxy, tetra-fluoroethylenedioxy, difluoromethylthio, trifluoromethylthio, trifluoromethylsulphinyl, trifluoromethylsulphonyl, benzyloxy, hydroxyl, nitro, mercapto, cyano or amino, or represents pyridyl which is optionally mono- or disubstituted by fluorine, chlorine, bromine, methyl, ethyl, methoxy, ethoxy, prop-oxy, i-propoxy or trifluoromethyl, or represents Ar², where Ar² represents Ar¹ which is additionally substituted by phenyl or phenoxy, where these substituents for their part are optionally mono- or disubstituted by fluorine, chlorine, bromine, methyl, ethyl, isopropyl, n-, s-, i- or t-butyl, methoxy, ethoxy, isopropoxy, n-, s-, i- or t-butoxy, trifluoromethyl, trifluoromethoxy, nitro or cyano.

Ar most preferably represents phenyl which is mono- or polysubstituted by trifluoromethyl, fluorine, chlorine, allyloxy, cyano, benzyloxy, or represents the group

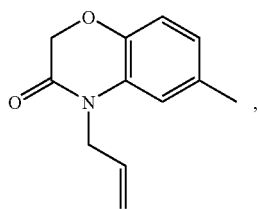, where particular emphasis is given to the meanings 4-chlorophenyl, 3,5-di(trifluoromethyl)phenyl and 2-fluoro-4-chloro-5-allyloxy.

X especially preferably represents CN.

Y especially preferably represents hydrogen, $C_1$–$C_6$-alkyl, $C_1$–$C_3$-halogeno-alkyl, cyclopropyl, cyclopentyl, cyclohexyl, cyclopropylmethyl, cyclopentylmethyl or cyclohexylmethyl.

Z especially preferably represents hydrogen or methyl.

Particular mention may also be made of the following sub-group of compounds of the formula (I):

2-enamino-ketonitriles of the general formula (I)',

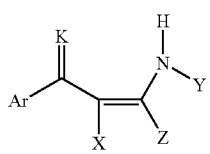

(I)' in which

K represents oxygen or sulphur,

Ar represents in each case substituted phenyl, naphthyl or represents in each case optionally substituted mono- or bicyclic hetaryl having 5 to 10 ring atoms, X represents CN,

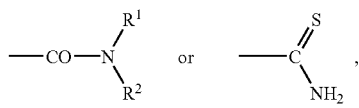

Y represents hydrogen, represents in each case optionally substituted alkyl, alkenyl, alkoxyalkyl, alkylthioalkyl, represents in each case optionally substituted cycloalkyl or cycloalkylalkyl which is interrupted in the cycle by heteroatoms or represents optionally substituted phenylalkyl or hetarylalkyl, Z represents hydrogen, represents in each case optionally substituted alkyl, phenyl or phenylalkyl, $R^1$ represents hydrogen, represents in each case optionally substituted saturated or unsaturated alkyl or cycloalkyl, each of which is optionally interrupted by heteroatoms, represents in each case optionally substituted phenyl or hetaryl, represents in each case optionally substituted phenylalkyl or hetarylalkyl, and $R^2$ represents hydrogen, represents in each case optionally substituted saturated or unsaturated alkyl or alkoxy, represents in each case optionally substituted phenyl, phenylalkyl or phenylalkyloxy, or $R^1$, $R^2$ furthermore together with the nitrogen atom to which they are attached may represent an optionally substituted cycle which is optionally interrupted by one or more heteroatoms.

For the compounds of the formula (I)', the following applies:

Ar preferably represents $Ar^1$, where $Ar^1$ represents phenyl, naphthyl or mono- or bicyclic hetaryl having five to ten ring atoms, each of which is optionally mono- to pentasubstituted by halogen, $C_1$–$C_8$-alkyl, $C_2$–$C_8$-alkenyl, $C_2$–$C_8$-alkinyl, $C_1$–$C_8$-alkoxy, $C_2$–$C_8$-alkenyloxy, $C_3$–$C_8$-alkinyloxy, $C_1$–$C_8$-alkylthio, $C_1$–$C_6$-alkylsulphonyl, $C_1$–$C_6$-halogenoalkyl, $C_1$–$C_6$-halogenoalkoxy, $C_2$–$C_8$-halogenoalkenyloxy, $C_1$–$C_2$-alkylidenediyl-dioxy, $C_1$–$C_2$-halogenoalkylidenediyl-dioxy, halogeno-$C_1$–$C_4$-alkylthio, halogeno-$C_1$–$C_4$-alkylsulphonyl, hydroxyl, mercapto, nitro, cyano, amino or by the groups a)

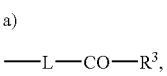

b)

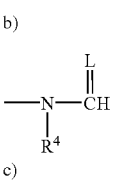

c)

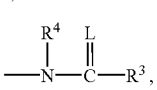

d)

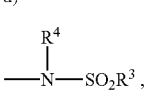

e)

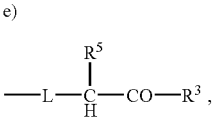

f)

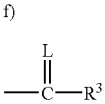

or represents $Ar^2$, where $Ar^2$ represents $Ar^1$ which is additionally substituted by phenyl, naphthyl, five- or six-membered hetaryl, phenyl-$C_1$–$C_4$-alkyl, phenoxy, phenyl-S(O)$_g$—, five- or six-membered hetaryloxy or hetaryl-S(O)$_g$, where these substituents for their part are each optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, where g represents 0, 1 or 2.

K preferably represents oxygen or sulphur.

L preferably represents oxygen or sulphur.

X preferably represents CN,

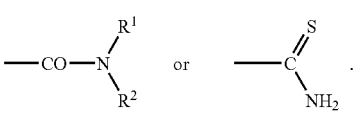

Y preferably represents hydrogen, $C_1$–$C_{12}$-alkyl, $C_3$–$C_{10}$-alkenyl, $C_1$–$C_6$-alkoxy-$C_2$–$C_4$-alkyl, $C_1$–$C_6$-alkylthio- $C_2$–$C_4$-alkyl, $C_1$–$C_8$-halogenoalkyl, represents in each case optionally $C_1$–$C_6$-alkyl-, $C_1$–$C_6$-alkoxy-, $C_1$–$C_4$-halogenoalkyl- or halogen-substituted $C_3$–$C_8$-cycloalkyl or $C_3$–$C_8$-cycloalkyl-$C_1$–$C_4$-alkyl, optionally interrupted in the cycle by oxygen or sulphur, represents phenyl-$C_1$–$C_4$-alkyl or five- or six-membered hetaryl-$C_1$–$C_4$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents hydrogen, $C_1$–$C_6$-alkyl, represents phenyl or phenyl-$C_1$–$C_4$-alkyl, each of which is optionally mono- to trisubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^1$ preferably represents hydrogen, represents in each case optionally fluorine and/or chlorine-substituted $C_1$–$C_{10}$-alkyl, $C_3$–$C_{10}$-alkenyl, $C_3$–$C_6$-alkinyl, represents in each case optionally fluorine-, chlorine-, $C_1$–$C_4$-alkyl-, $C_1$–$C_4$-alkoxy-substituted $C_3$–$C_8$-cycloalkyl or $C_5$–$C_8$-cycloalkenyl in which optionally one methylene group may be replaced by oxygen or sulphur, or represents phenyl, pyridyl, thienyl, pyrimidyl, thiazolyl, phenyl-$C_1$–$C_4$-alkyl, pyridyl-$C_1$–$C_2$-alkyl, thiazolyl-$C_1$–$C_2$-alkyl, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^2$ preferably represents hydrogen, $C_1$–$C_6$-alkyl or $C_3$–$C_6$-alkenyl.

$R^1$, $R^2$ furthermore together with the nitrogen atom to which they are attached preferably represent an in each case optionally $C_1$–$C_4$-alkyl-substituted five- to eight-membered cycle in which optionally one methylene group may be replaced by oxygen or sulphur.

$R^3$ preferably represents in each case optionally fluorine- and/or chlorine-substituted $C_1$–$C_{10}$-alkyl, $C_2$–$C_{10}$-alkenyl, $C_3$–$C_{10}$-alkinyl, $C_1$–$C_{10}$-alkoxy, $C_1$–$C_4$-alkoxy-$C_1$–$C_4$-alkyl, $C_1$–$C_4$-alkylthio-$C_1$–$C_4$-alkyl, in each case optionally fluorine, chlorine, $C_1$–$C_4$-alkyl and/or $C_1$–$C_4$-alkoxy-substituted $C_3$–$C_8$-cycloalkyl or $C_3$–$C_8$-cycloalkoxy in which optionally one methylene group may be replaced by oxygen or sulphur, represents phenyl, phenoxy, benzyloxy, five- or six-membered hetaryl or phenyl-$C_1$–$C_4$-alkyl, each of which may optionally be mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, or, in the case of the radicals a), c) and f) mentioned under Ar, also represents a group

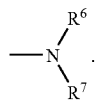

$R^4$ preferably represents hydrogen or $C_1$–$C_4$-alkyl.

$R^5$ preferably represents hydrogen or optionally fluorine- and/or chlorine-substituted $C_1$–$C_4$-alkyl.

$R^6$ preferably represents hydrogen, in each case optionally fluorine- and/or chlorine-substituted $C_1$–$C_{10}$-alkyl, $C_3$–$C_8$-alkenyl, $C_3$–$C_8$-alkinyl, $C_1$–$C_{10}$-alkoxy, $C_3$–$C_8$-alkenyloxy, optionally fluorine-, chlorine-, $C_1$–$C_4$-alkyl or $C_1$–$C_4$-alkoxy-substituted $C_3$–$C_8$-cycloalkyl in which optionally one methylene group may be replaced by oxygen or sulphur, represents phenyl, phenyl-$C_1$–$C_4$-alkyl or phenyl-$C_1$–$C_2$-alkoxy, each of which is optionally mono- to tetrasubstituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^7$ preferably represents hydrogen, $C_1$–$C_6$-alkyl or $C_3$–$C_6$-alkenyl.

$R^6$, $R^7$ furthermore together with the nitrogen atom to which they are attached preferably represent an optionally $C_1$–$C_4$-alkyl-substituted five- to eight-membered cycle in which optionally one methylene group may be replaced by oxygen or sulphur.

For the compounds of the formula (I)', the following applies:

K particularly preferably represents oxygen or sulphur.

Ar particularly preferably represents $Ar^1$, where $Ar^1$ represents phenyl, naphthyl, quinolinyl, thienyl, pyrimidyl, furanyl, thiazolyl, benzothiazolyl, oxazolyl, pyrazolyl or pyridyl, each of which is optionally mono- to trisubstituted by fluorine, chlorine, bromine, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_3$–$C_6$-alkinyloxy, $C_1$–$C_6$-alkylthio, $C_1$–$C_4$-alkylsulphonyl, $C_1$–$C_4$-halogenoalkyl, $C_1$–$C_4$-halogenoalkoxy, $C_2$–$C_4$-halogenoalkenyloxy, $C_1$–$C_2$-alkylidenediyl-dioxy, $C_1$–$C_2$-halogenoalkylidenediyl-dioxy, halogeno-$C_1$–$C_2$-alkylthio, halogeno-$C_1$–$C_2$-alkylsulphonyl, hydroxyl, mercapto, nitro, cyano, amino or by one of the following groups a)

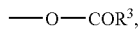

b)

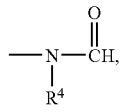

c)

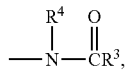

d)

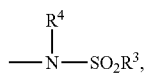

e)

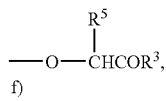

f)

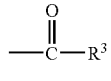

or represents $Ar^2$, where $Ar^2$ represents $Ar^1$ which is additionally substituted by phenyl, pyridyl, pyrimidyl, thienyl, furanyl, thiazolyl, tetrazolyl, triazolyl, benzyl, phenoxy, phenyl-S(O)$_g$—, pyridyloxy, pyrimidyloxy, thiazolyloxy, pyridyl-S(O)$_g$—, pyrimidyl-S(O)$_g$— or thiazolyl-S(O)$_g$—, where these substituents for their part are optionally mono- to trisubstituted by fluorine, chlorine, bromine, $C_1$–$C_4$-alkyl, $C_2$–$C_4$-alkenyl, $C_1$–$C_4$-alkoxy, $C_1$–$C_2$-halogenoalkyl, $C_1$–$C_2$-halogenoalkoxy, nitro or cyano, where g represents 0, 1 or 2.

X particularly preferably represents CN,

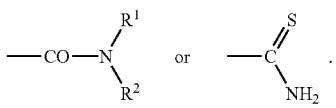

Y particularly preferably represents hydrogen, $C_1$–$C_{10}$-alkyl, $C_1$–$C_6$-halogenoalkyl, $C_3$–$C_8$-alkenyl, $C_1$–$C_4$-alkoxy-$C_2$–$C_3$-alkyl, $C_1$–$C_4$-alkylthio-$C_2$–$C_3$-alkyl, represents optionally $C_1$–$C_4$-alkyl-, $C_1$–$C_4$-alkoxy-, $C_1$–$C_2$-halogenoalkyl-, fluorine- or chlorine-substituted $C_3$–$C_6$-cycloalkyl or $C_3$–$C_6$-cycloalkyl-$C_1$–$C_2$-alkyl, represents phenyl-$C_1$–$C_2$-alkyl, thiazolylmethyl or pyridylmethyl, each of which is optionally mono- to trisubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents hydrogen, $C_1$–$C_3$-alkyl, represents phenyl or benzyl, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

$R^1$ particularly preferably represents hydrogen, represents in each case optionally fluorine- and/or chlorine-substituted $C_1$–$C_6$-alkyl, $C_2$–$C_6$-alkenyl, $C_3$–$C_4$-alkinyl, represents optionally fluorine-, chlorine-, $C_1$–$C_2$-alkyl-, $C_1$–$C_2$-alkoxy-substituted $C_3$–$C_6$-cycloalkyl or represents phenyl or benzyl, each of which is optionally mono- or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

$R^2$ particularly preferably represents hydrogen, represents in each case optionally fluorine- and/or chlorine-substituted $C_1$–$C_4$-alkyl or $C_3$–$C_4$-alkenyl.

$R^1$, $R^2$ furthermore together with the nitrogen atom to which they are attached particularly preferably represent an optionally methyl-substituted five- or six-membered cycle in which optionally one methylene group may be replaced by oxygen.

$R^3$ particularly preferably represents in each case optionally fluorine- and/or chlorine-substituted $C_1$–$C_6$-alkyl, $C_2$–$C_6$-alkenyl, $C_3$–$C_6$-alkinyl, $C_1$–$C_6$-alkoxy, $C_1$–$C_4$-alkoxy-$C_1$–$C_2$-alkyl, $C_1$–$C_4$-alkylthio-$C_1$–$C_2$-alkyl, in each case optionally fluorine-, chlorine-, $C_1$–$C_2$-alkyl- and/or $C_1$–$C_2$-alkoxy-substituted $C_3$–$C_6$-cycloalkyl or $C_3$–$C_6$-cycloalkoxy in which optionally one methylene group may be replaced by oxygen, represents phenyl, phenoxy, benzyloxy, thienyl, furanyl, pyridyl, pyrimidyl, thiazolyl, pyrazolyl or phenyl-$C_1$–$C_2$-alkyl, each of which may optionally be mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro, or, in the case of the radicals a), c) and f) mentioned under Ar, also represents a group

$R^4$ particularly preferably represents hydrogen.
$R^5$ particularly preferably represents hydrogen, methyl or ethyl.

$R^6$ particularly preferably represents hydrogen, in each case optionally fluorine-and/or chlorine-substituted $C_1$–$C_6$-alkyl, $C_3$–$C_6$-alkenyl, $C_3$–$C_6$-alkinyl, $C_1$–$C_6$-alkoxy, $C_3$–$C_6$-cycloalkyl, in which optionally one methylene group may be replaced by oxygen, represents phenyl or phenyl-$C_1$–$C_2$-alkyl, each of which is optionally mono- or disubstituted by fluorine, chlorine, bromine, $C_1$–$C_4$-alkyl, $C_1$–$C_4$-alkoxy, trifluoromethyl, difluoromethoxy, trifluoromethoxy, cyano or nitro.

$R^7$ particularly preferably represents hydrogen or $C_1$–$C_4$-alkyl.

$R^6$, $R^7$ furthermore together with the nitrogen atom to which they are attached particularly preferably represent an optionally $C_1$–$C_2$-alkyl-substituted five- or six-membered cycle in which optionally one methylene group may be replaced by oxygen.

For the compounds of the formula (I)', the following applies:

K very particularly preferably represents oxygen or sulphur.

Ar very particularly preferably represents $Ar^1$, where $Ar^1$ represents phenyl which is optionally mono- to trisubstituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, mercapto, nitro, cyano or amino, or represents pyridyl which is optionally mono- or disubstituted by fluorine, chlorine, bromine, methyl, ethyl, methoxy, ethoxy, propoxy, i-propoxy, butoxy, i-butoxy, methylthio, ethylthio or trifluoromethyl, or represents $Ar^2$, where $Ar^2$ represents $Ar^1$ which is additionally substituted by phenyl, pyridyl, thienyl, tetrazolyl, triazolyl or phenoxy, where these substituents for their part are optionally mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano.

X very particularly preferably represents —CN, —CO—NH$_2$, or

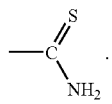

Y very particularly preferably represents hydrogen, $C_1$–$C_6$-alkyl, $C_1$–$C_4$-halogenoalkyl, allyl, 3-butenyl, $C_1$–$C_4$-alkoxy-$C_2$-alkyl, represents in each case optionally methyl-, methoxy-, trifluoromethyl-, fluorine- or chlorine-substituted cyclopropyl, cyclopentyl, cyclohexyl, cyclopropylmethyl, cyclopentylmethyl, cyclohexylmethyl or represents benzyl which is optionally mono- or disubstituted by fluorine, chlorine, bromine, methoxy, methyl, trifluoromethyl, trifluoromethoxy, cyano or nitro or represents optionally chlorine-substituted pyridylmethyl or triazolylmethyl.

Z very particularly preferably represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro.

R³ very particularly preferably represents methyl, ethyl, propyl, isopropyl, n-, s-, i- or t-butyl, vinyl, trifluoromethyl, methoxy, ethoxy, propoxy, isopropoxy, n-, s-, i- or t-butyloxy, cyclopropyl, cyclopentyl, cyclohexyl, cyclopentyloxy, cyclohexyloxy, represents phenyl, pyridyl or benzyl, each of which is optionally mono- or disubstituted by fluorine, chlorine, bromine, methyl, n-, s-, i- or t-butyl, methoxy, trifluoromethyl, trifluoromethoxy, cyano or nitro, or, in the case of the radicals a), c) and f) mentioned under Ar, also represents a group

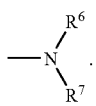

R⁵ very particularly preferably represents hydrogen or methyl.

R⁶ very particularly preferably represents hydrogen, methyl, ethyl, propyl, isopropyl, n-, s-, i- or t-butyl, cyclopropyl, cyclopentyl, cyclohexyl, represents phenyl which is optionally mono- or disubstituted by fluorine, chlorine, bromine, methyl, methoxy, trifluoromethyl, trifluoromethoxy, cyano or nitro.

R⁷ very particularly preferably represents hydrogen, methyl or ethyl.

R⁶, R⁷ together with the nitrogen atom to which they are attached very particularly preferably represent a pyrrolidine, piperidine or morpholine radical.

For the compounds of the formula (I)', the following applies:

K especially preferably represents oxygen.

Ar especially preferably represents Ar¹, where Ar¹ represents phenyl which is optionally mono- to trisubstituted by fluorine, chlorine, bromine, methyl, ethyl, propyl, isopropyl, n-, s-, i- or t-butyl, methoxy, ethoxy, propoxy, isopropoxy, n-, s-, i- or t-butoxy, allyloxy, methallyloxy, 2-butenyloxy, propargyloxy, 2-butinyloxy, methylthio, ethylthio, methylsulphinyl, ethylsulphinyl, methylsulphonyl, ethylsulphonyl, trifluoromethyl, difluoromethoxy, trifluoromethoxy, methylenedioxy, difluoromethylenedioxy, tetrafluoroethylenedioxy, difluoromethylthio, trifluoromethylthio, trifluoromethylsulphinyl, trifluoromethylsulphonyl, hydroxyl, nitro, mercapto, cyano or amino or represents pyridyl which is optionally mono- or disubstituted by fluorine, chlorine, bromine, methyl, ethyl, methoxy, ethoxy, propoxy, i-propoxy or trifluoromethyl,
or represents Ar², where Ar² represents Ar¹ which is additionally substituted by phenyl or phenoxy, where these substituents for their part are optionally mono- or disubstituted by fluorine, chlorine, bromine, methyl, ethyl, isopropyl, n-, s-, i- or t-butyl, methoxy, ethoxy, isopropoxy, n-, s-, i- or t-butoxy, trifluoromethyl, trifluoromethoxy, nitro or cyano.

X especially preferably represents CN.

Y especially preferably represents hydrogen, $C_1$–$C_6$-alkyl, $C_1$–$C_3$-halogenoalkyl, cyclopropyl, cyclopentyl, cyclohexyl, cyclopropylmethyl, cyclopentyl-methyl or cyclohexylmethyl.

Z especially preferably represents hydrogen or methyl.

All of the abovementioned compounds of the formula (I) can be present both as cis and as trans isomers. To simplify the presentation, in each case only one isomer is shown in the formulae of the compounds. However, the respective other isomer is likewise included in the invention.

The abovementioned general or preferred radical definitions apply both to the end products of the formula (I) and, correspondingly, to the starting materials and intermediates required in each case for the preparation. These radical definitions can be combined with one another as desired, i.e. including combinations between the given preferred ranges.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Especial preference according to the invention is given to the compounds of the formula (I) which contain a combination listed above as being especially preferred.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitution, the substituents can be identical or different.

It has been found that the novel compounds of the formula (I) are obtained by the process described below:

(A) Compounds of the formula (I)

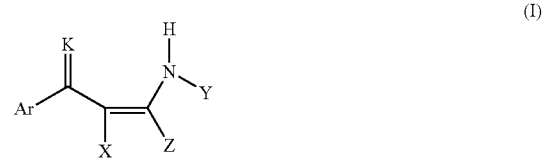

in which
Ar, X, Y and Z are each as defined above and
K represents oxygen
are obtained when
compounds of the formula (II)

in which
Ar and X are each as defined above,
are reacted with compounds of the formula (III)

in which
Y and Z are each as defined above but do not represent hydrogen and

W represents O or S(O)$_g$, where g represents 0 or 2, and

R$^8$ represents alkyl, in particular C$_1$–C$_6$-alkyl, or benzyl, if appropriate in the presence of a diluent and if appropriate in the presence of a base or an acid and/or a metal compound of the formula (IV)

 (IV)

in which

Me represents a divalent transition metal atom, in particular nickel, and

V represents a chelate ligand, in particular a bidentate chelate ligand, such as, for example, acetylacetonate (R. G. Glushkov et al., Khim.-Farm. Zh. 24, (7), (1990), 24–27; M. V. Mezentseva et al., Khim.-Farm. Zh. 25, (12), (1991), 19–23; G. Dannhardt, A. Bauer, Pharmazie 51, (1996), 805–810).

(B) Moreover, it has been found that compounds of the formula (I)

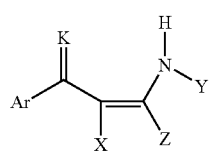 (I)

in which

Ar, X, Y and Z are each as defined above and

K represents oxygen, are obtained when compounds of the formula (V)

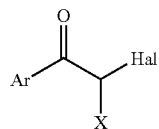 (V)

in which

Ar and X are each as defined above, and

Hal represents halogen, in particular chlorine or bromine, are reacted with compounds of the formula (VI)

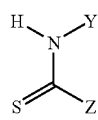 (VI)

in which

Y and Z are each as defined above, but do not represent hydrogen, if appropriate in the presence of a diluent, to give compounds of the formula (VII)

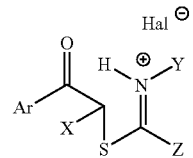 (VII)

in which

Ar, X, Y and Z are each as defined above which are reacted further, if appropriate in the presence of a base and if appropriate in the presence of a trivalent phosphorus compound (for example triphenylphosphine, triethyl phosphite), with elimination of sulphur and hydrogen halide, to give compounds of the formula (I)

in which

Ar, X, Y and Z are each as defined above (see A. Eschenmoser et al., Helv. Chim. Acta 54, (1971), 710–734; V. Issartel et al., C.R. Acad. Sci., Ser. II, Mec., Phys., Chim., Astron. 321, (12), (1995), 521–524).

(C) Furthermore, it has been found that compounds of the formula (I)

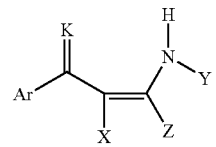 (I)

in which

Ar, X, Y and Z are each as defined above and K represents oxygen, are obtained when compounds of the formula (II)

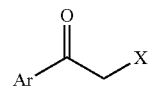 (II)

in which

Ar and X are each as defined above, are initially condensed with compounds of the formula (VIII)

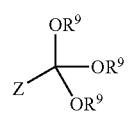 (VIII)

in which

Z is as defined above and

R$^9$ represents C$_1$–C$_4$-alkyl, preferably methyl and ethyl, and the resulting intermediates are, preferably without intermediate isolation, reacted with amines of the formula (IX)

 (IX)

in which

Y is as defined above, if appropriate in the presence of a diluent and if appropriate in the presence of a base.

(D) Furthermore, it has been found that compounds of the formula (I)

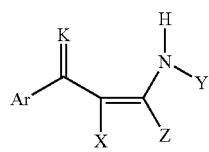 (I)

in which

Ar, X, Y and Z are each as defined above and

K represents sulphur, are obtained when compounds of the formula (I)

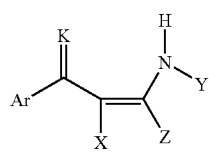 (I)

in which

Ar, X, Y and Z are each as defined above and

K represents oxygen are reacted in the presence of a sulphurizing agent, such as, for example, phosphorus pentasulphide or 2,4-bis(4-methoxyphenyl)-1,2,3,4-dithiaphosphetane 2,4-disulphide (Lawesson's reagent) in the presence of a solvent.

(E) Moreover, it has been found that compounds of the formula (I)

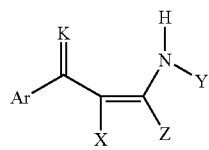 (I)

in which

Ar, X, Y and Z are each as defined above,

Ar has the meaning given above for $Ar^2$ and

K represents oxygen, are obtained when compounds of the formula ($I^1$)

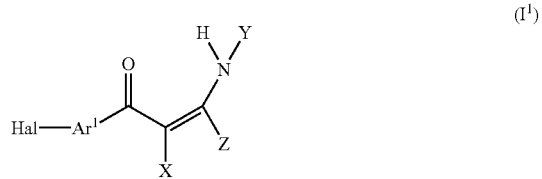 ($I^1$)

in which $Ar^1$, X, Y and Z are each as defined above and

Hal represents halogen, in particular bromine, are reacted with boronic acids of the formula (X)

$Ar^{2'}$—B(OH)$_2$ (X), in which $Ar^{2'}$ represents the substituents which have been mentioned above under $Ar^2$ as additional substituents for $Ar^1$, in the presence of a solvent, if appropriate in the presence of a base and a noble metal complex, preferably a palladium complex.

Using, according to process A, for example 4-methylbenzoylacetonitrile and methyl N-ethyliminoacetate as starting materials, the course of the reaction can be represented by the following reaction scheme:

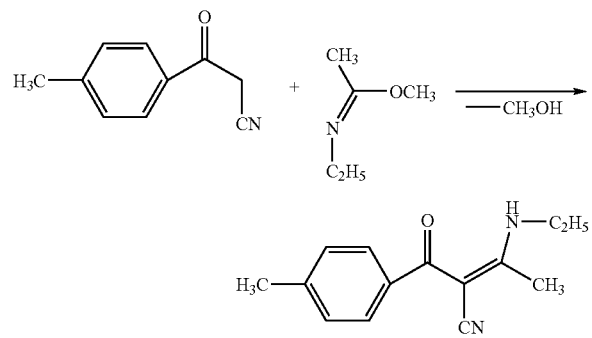

Using, according to process B, for example 2-bromo-2-(3-chlorobenzoyl)acetonitrile and N-methylthiobenzamide as starting materials, the course of the reaction can be represented by the following reaction scheme:

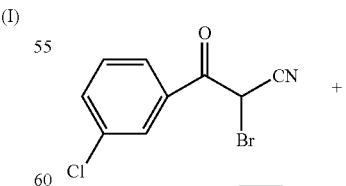

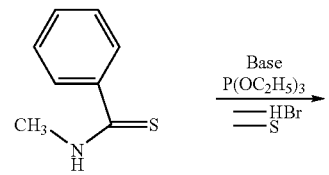

-continued

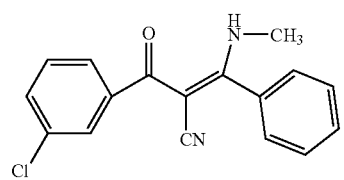

Using, according to process C, for example 3,4-dichloro-benzoyl-acetonitrile, methyl orthoacetate and isopropylamine as starting materials, the course of the reaction can be represented by the following reaction scheme:

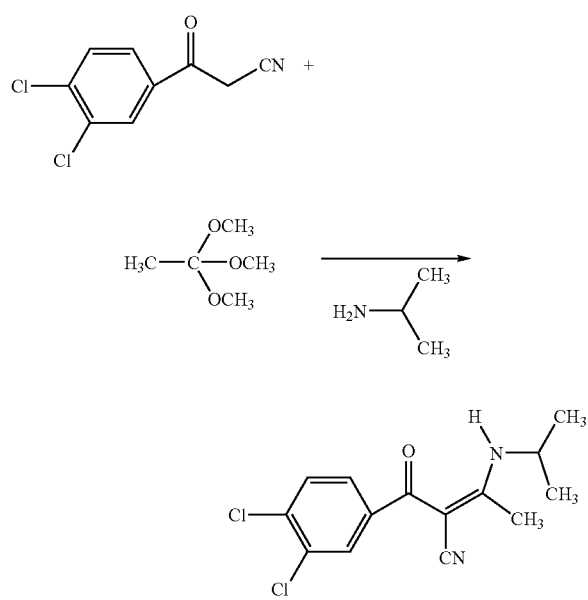

Using, according to process D, for example Z-2-(4-trifluoromethyl-benzoyl)-3-(N-ethylamino)crotononitrile and Lawesson's reagent as starting materials, the course of the reaction can be represented by the following reaction scheme:

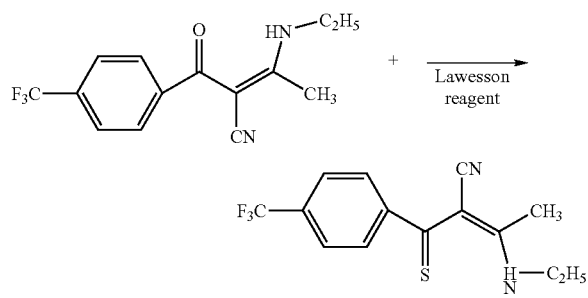

Using, according to process E, for example 2-(4-bromo-benzoyl)-3-(N-methylamino)crotononitrile and 4-chloro-phenylboronic acid as starting materials, the course of the reaction can be represented by the following reaction scheme:

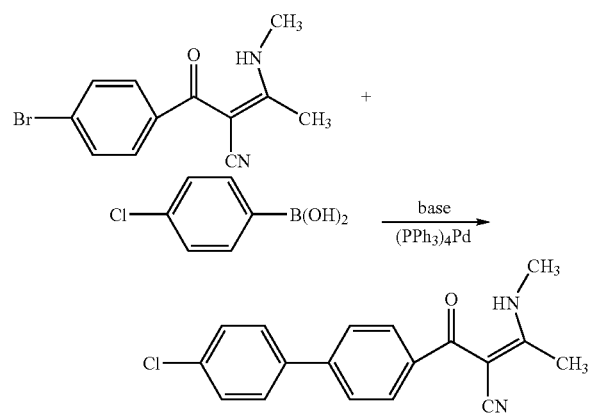

The compounds of the formula (II)

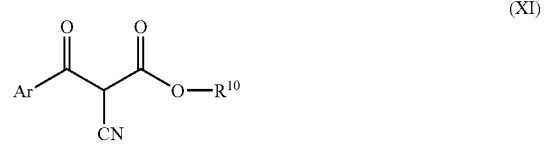

(II)

in which

Ar, X are each as defined above, required as starting materials in process (A) are known or can be prepared by processes known in principle from the literature (Organikum, 16th revised edition, pp. 415, 417, VEB Deutscher Verlag der Wissenschaften, Berlin 1986, German Patent Applications with the application numbers 198 519 86 and 10 007 286 and WO 00/27 812).

The compounds of the formula (II) are obtained, for example, by hydrolysing compounds of the formula (XI)

(XI)

in which

Ar is as defined above, $R^{10}$ represents alkyl, in particular $C_1$–$C_6$-alkyl, or benzyl, which may optionally be substituted, in the presence of an acid (for example an inorganic acid, such as hydrochloric acid) or a base (for example an alkali metal hydroxide, such as sodium hydroxide or potassium hydroxide) and if appropriate in the presence of a diluent (for example an aqueous alcohol, such as methanol or ethanol), at temperatures between 0° C. and 200° C., preferably between 20° C. and 150° C., followed by decarboxylation, where the elimination of the radical may optionally also be carried out hydrolytically by known processes (Bowman, Fordham, J. Chem. Soc. 1951, 2758) using molecular hydrogen at pressures between 1 and 100 bar, if appropriate in the presence of a solvent, such as, for example, methanol, ethanol or ethyl acetate, at temperatures between –20 and 100° C., preferably at room temperature, in the presence of a transition metal, such as, for example, palladium, nickel, rhodium or platinum, which is optionally immobilized on a support, such as, for example, activated carbon or barium sulphate.

The compounds of the formula (XI) can be prepared by known processes (Organikum, 16th revised edition, p. 480, VEB Deutscher Verlag der Wissenschaften, Berlin 1986).

The compounds of the formula (XI) are obtained, for example, by reacting compounds of the formula (XII)

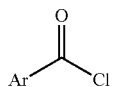

(XII)

in which

Ar is as defined above, with cyanoacetic acid esters of the formula (XIII)

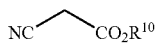

(XIII)

in which $R^{10}$ represents alkyl, in particular $C_1$–$C_6$-alkyl, or benzyl, in the presence of a base (for example a metal alkoxide, such as sodium methoxide or sodium ethoxide) and if appropriate in the presence of a diluent (for example ether or the alcohol which is derived from the alkoxide), at temperatures of from 0° C. to 150° C., preferably between 20 and 120° C.

Some of the compounds of the formula (XII) are novel, and they can be prepared by processes known in principle (for example Organikum, 16th revised edition, p. 423, VEB Deutscher Verlag der Wissenschaften, Berlin 1986).

The compounds of the formula (XII) are obtained, for example, by reacting compounds of the formula (XIV)

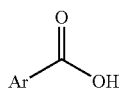

(XIV)

in which

Ar is as defined above, with halogenating agents (for example thionyl chloride, phosgene, phosphorus trichloride), if appropriate in the presence of a diluent (for example optionally chlorinated aliphatic or aromatic hydrocarbons, such as toluene or methylene chloride), at temperatures of from 0° C. to 150° C., preferably between 20° C. and 100° C.

Cyanoacetic acid esters of the formula (XIII) are known compounds of organic chemistry.

Some of the compounds of the general formula (XIV-b)

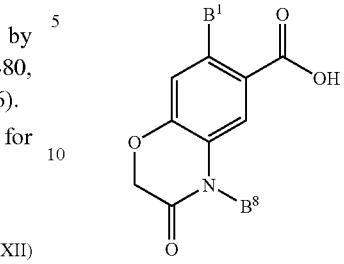

(XIV-b)

in which $B^1$ represents hydrogen or fluorine and $B^8$ represents hydrogen, hydroxyl, represents in each case optionally cyano-, halogen-, alkoxy-, alkylcarbonyl- or alkoxycarbonyl-substituted alkyl, alkylcarbonyl alkoxycarbonyl, alkylthio or alkylsulphonyl, represents in each case optionally halogen-substituted alkenyl or alkinyl, represents in each case optionally halogen- or alkyl-substituted cycloalkyl or cycloalkylalkyl, represents in each case optionally halogen-substituted alkoxy or alkenyloxy, represents in each case optionally cyano-, halogen-, alkyl-, halogenoalkyl-, alkoxy- or halogenoalkoxy-substituted arylalkyl or arylalkoxy, are known, or they can be synthesized by known processes.

Here, $B^8$ preferably represents hydrogen, hydroxyl, represents in each case optionally cyano-, halogen-, $C_1$–$C_4$-alkoxy-, $C_1$–$C_4$-alkylcarbonyl- or $C_1$–$C_4$-alkoxycarbonyl-substituted $C_1$–$C_8$-alkyl, $C_1$–$C_8$-alkylcarbonyl, $C_1$–$C_8$-alkoxycarbonyl, $C_1$–$C_8$-alkylthio or $C_1$–$C_8$-alkylsulphonyl, represents in each case optionally halogen-substituted $C_2$–$C_6$-alkenyl or $C_2$–$C_6$-alkinyl, represents in each case optionally halogen- or $C_1$–$C_4$-alkyl-substituted $C_3$–$C_8$-cycloalkyl or $C_3$–$C_8$-cycloalkyl-$C_1$–$C_4$-alkyl, represents in each case optionally halogen-substituted $C_1$–$C_8$-alkoxy or $C_2$–$C_8$-alkenyloxy, represents in each case optionally cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl-$C_1$–$C_4$-alkyl or penyl-$C_1$–$C_4$-alkoxy.

The novel compounds are obtained, inter alia, by converting compounds of the general formula (XV)

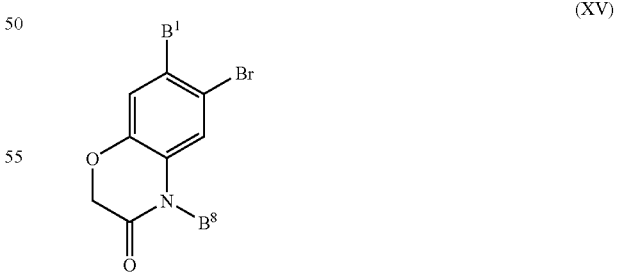

(XV)

in which $B^1$ represents hydrogen or fluorine and $B^8$ is as defined above, by processes known per se using $CO_2$ in the presence of organometallic compounds into compounds of the general formula (XIV-b) (for example Organikum, 16th revised edition, p.499, VEB Deutscher Verlag der Wissenschaften 1986).

Suitable for use as organometallic bases are, in addition to organomagnesium compounds, also organolithium compounds, which are known chemicals for synthesis of organic chemistry. Suitable solvents/diluents are hydrocarbons (such as toluene) or ethers (such as, for example, tetrahydrofuran or diethyl ether). It is also possible to use mixtures of the abovementioned solvents.

The reaction temperature is usually between −100° C. and 80° C., preferably between −80° C. and 25° C. (room temperature). For work-up, the reaction mixture is diluted with water or an inorganic acid, such as, for example, hydrochloric acid, which may be diluted or concentrated, and the product is isolated using a water-immiscible solvent and purified by customary methods, for example by crystallization.

Some of the compounds of the general formula (XV) in which
$B^1$ represents hydrogen or fluorine and
$B^8$ is as defined above, are novel, and they can be synthesized by known processes (Sicker et al., Tetrahedron, 31, (1996), 10389; Bell et al., J. Med. Chem., 33, (1990), 380).

The novel compounds of the formula (XV) in which
$B^1$ represents hydrogen or fluorine and
$B^8$ represents in each case optionally cyano-, halogen-, alkoxy-, alkylcarbonyl- or alkoxycarbonyl-substituted alkyl, alkylcarbonyl, alkoxycarbonyl, alkylthio or alkylsulphonyl, represents in each case optionally halogen-substituted alkenyl or alkinyl, represents in each case optionally halogen- or alkyl-substituted cycloalkyl or cycloalkylalkyl, represents in each case optionally cyano-, halogen-, alkyl-, halogenoalkyl-, alkoxy- or halogenoalkoxy-substituted arylalkyl, are obtained, inter alia, from compounds of the general formula (XV)′

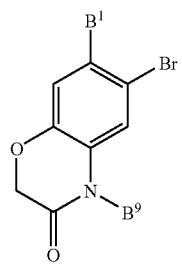

(XV)′ in which $B^1$ represents hydrogen or fluorine and $B^9$ represents hydrogen, by reaction with an alkylating agent of the formula (XVI)

$$B^8\text{—}X^1 \qquad (XVI),$$

in which
$B^8$ represents in each case optionally cyano-, halogen-, alkoxy-, alkylcarbonyl- or alkoxycarbonyl-substituted alkyl, alkylcarbonyl, alkoxycarbonyl, alkylthio or alkylsulphonyl, represents in each case optionally halogen-substituted alkenyl or alkinyl, represents in each case optionally halogen- or alkyl-substituted cycloalkyl or cycloalkylalkyl, represents in each case optionally cyano-, halogen-, alkyl-, halogenoalkyl-, alkoxy- or halogenoalkoxy-substituted arylalkyl and
$X^1$ represents halogen, in particular iodine, bromine or chlorine, or other leaving groups, for example activated esters, such as mesylate or tosylate, or from compounds of the general formula (XV)′ in which $B^1$ represents hydrogen or fluorine and $B^9$ represents hydroxyl, by reaction with an alkylating agent of the formula (XVII)′

$$B^{10}\text{—}X^1 \qquad (XVII)',$$

in which
$B^{10}$ represents in each case optionally halogen-substituted alkyl or alkenyl or represents in each case optionally cyano-, halogen-, alkyl-, halogenoalkyl-, alkoxy- or halogenoalkoxy-substituted arylalkyl and
$X^1$ represents halogen, in particular iodine, bromine or chlorine, or other leaving groups, for example activated esters, such as mesylate or tosylate, if appropriate in the presence of a base and in the presence of a solvent.

Bases suitable for use in the reaction are, in addition to alkali metal oxides and alkaline earth metal oxides, tertiary amines, such as triethylamine, pyridine or N,N-diethylaniline, which may be used in molar ratios or else in excess.

Suitable solvents or diluents are, in addition to hydrocarbons such as toluene, also halogenated hydrocarbons, such as dichloromethane. It is possible to use polar aprotic solvents/diluents, such as dimethylformamide, and also mixtures of the abovementioned solvents. The reaction temperature is usually between the melting point and the boiling point of the reaction mixture, preferably between −10° C. and 80° C.

The compounds of the general formula (XV)′, in which $B^1$ represents hydrogen or fluorine and $B^9$ represents hydrogen are known from the literature (Huang et al., Synthesis (1984), 851; JP 63132881) and can be converted by oxidation according to processes known per se into compounds of the general formula (XV)′ in which $B^1$ represents hydrogen or fluorine and $B^9$ represents hydroxyl (P. G. Sammes et al., J. Chem. Soc., Perkin Trans I, (1979), 2481).

Furthermore, compounds of the general formula (XIV-b) in which
$B^1$ represents hydrogen or fluorine and
$B^8$ is as defined above, can be obtained by hydrolysing compounds of the formula (XVIII)

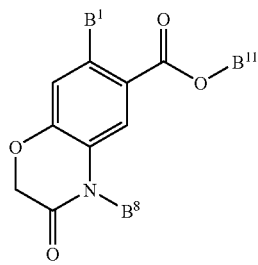

(XVIII)

in which
$B^1$ represents hydrogen or fluorine,
$B^8$ is as defined above and $B^{11}$ represents alkyl or benzyl, in particular $C_1$–$C_6$-alkyl or benzyl, which may optionally be fully or partially substituted by the radicals $R^1$ or $R^2$, in the presence of an acid (for example an inorganic acid, such as hydrochloric acid) or a base (for example an alkali metal hydroxide, such as sodium hydroxide or potassium hydroxide) and if appropriate in the presence of a diluent (for example an aqueous alcohol, such as methanol or ethanol), at temperatures between 0° C. and 200° C., preferably between 20° C. and 150° C. The radical $B^{11}$ can optionally also be removed hydrogenolytically using molecular hydrogen at pressures between 1 and 100 bar, if appropriate in the presence of a solvent, for example methanol, ethanol or ethyl acetate, at temperatures between −10° C. and 100° C., preferably at room temperature, in the presence of a transition metal, for example palladium, nickel, rhodium or platinum, which may optionally be immobilized on a support, such as activated carbon or barium sulphate, using known processes (Bowman, Fordham J. Chem. Soc., 1951, 2758).

Furthermore, compounds of the general formula (XVIII) in which
$B^1$ represents hydrogen or fluorine and
$B^8$ is as defined above and
$B^{11}$ represents hydrogen, alkyl or benzyl, in particular $C_1$–$C_6$-alkyl or benzyl, which may optionally in each case be fully or partially substituted by the radicals $R^1$ or $R^2$, can be obtained according to customary processes known per se, by reacting compounds of the general formula (XV) in which
$B^1$ represents hydrogen or fluorine and
$B^8$ is as defined above, with a nucleophile of the general formula (XIX)

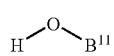

(XIX)

in which
$B^{11}$ represents hydrogen, alkyl or benzyl, in particular $C_1$–$C_6$-alkyl or benzyl, which may optionally in each case be fully or partially substituted by the radicals $R^1$ or $R^2$, in the presence of CO at pressures of from 1 bar to 100 bar, preferably between 1 bar and 50 bar, and at temperatures between 20° C. and 300° C., preferably between 20° C. and 150° C., in the presence of a catalyst, for example palladium salts or cobalt salts or transition metal carbonyl compounds, such as, for example, $Co_2(CO)_8$, if appropriate in the presence of a ligand (such as, for example, triphenylphosphine, trisodium (3-sulphonylphenyl)phosphine, in the presence of a base (for example an alkali metal hydroxide, such as sodium hydroxide or potassium hydroxide, or else organic bases, such as triethylamine or pyridine) and of a diluent (for example alcohols, water, tetrahydrofuran, dichloromethane, toluene or mixtures of the abovementioned diluents). The reaction can optionally also be carried out in the presence of phase-transfer catalysts (for example glycols, crown ethers or ammonium salts, such as tetrabutylammonium bromide or chloride) or auxiliaries (for example zeolites) or under irradiation with light, according to known processes (Ziolkowski et al., J. Mol. Catal. A: Chem., 154, (2000), 93; P. Kalck et al., J. Organomet. Chem., 482, (1994), 45; Du Pont de Nemours & Co U.S. Pat. No. 2,734,912; Alper, H. et al., Angew. Chem., 96, (1984), 710; Takatori K. et al., Tetrahedron, 54, (1998), 15861).

Furthermore, compounds of the general formula (XIV-b)

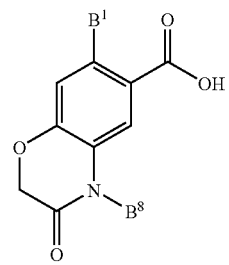

(XIV-b)

in which
$B^1$ represents hydrogen or fluorine and
$B^8$ represents in each case optionally cyano-, halogen-, alkoxy-, alkylcarbonyl- or alkoxycarbonyl-substituted alkyl, alkylcarbonyl, alkoxycarbonyl, alkylthio or alkylsulphonyl, represents in each case optionally halogen-substituted alkenyl or alkinyl, represents in each case optionally halogen- or alkyl-substituted cycloalkyl or cycloalkylalkyl, represents in each case optionally cyano-, halogen-, alkyl-, halogenoalkyl-, alkoxy- or halogenoalkoxy-substituted arylalkyl, can be obtained from compounds of the general formula (XIV-b),
in which
$B^1$ represents hydrogen or fluorine and
$B^8$ represents hydrogen, by reaction with an alkylating agent of the formula (XVII)'

(XVII)' in which
$B^{10}$ represents in each case optionally halogen-substituted alkyl or alkenyl or represents in each case optionally cyano-, halogen-, alkyl-, halogenoalkyl-, alkoxy- or halogenoalkoxy-substituted arylalkyl and
$X^1$ represents halogen, in particular iodine, bromine or chlorine, or other leaving groups, for example activated esters, such as mesylate or tosylate, if appropriate in the presence of a base and in the presence of a solvent.

Bases suitable for use in the reaction are, in addition to alkali metal oxides and alkaline earth metal oxides, tertiary amines such as triethylamine, pyridine or N,N-diethylaniline, which can be used in molar ratios or else in excess. Suitable solvents are, in addition to hydrocarbons such as toluene, also halogenated hydrocarbons, such as dichloromethane. It is possible to use polar aprotic solvents/diluents, such as dimethylformamide, and also mixtures of the abovementioned solvents. The reaction temperature is usually between the melting point and the boiling point of the reaction mixture, preferably between −10° C. and 80° C.

Some of the compounds of the formula (III)

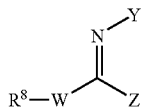

(III)

in which

W, Y, Z and R⁸ are each as defined above, likewise required as starting materials are known, and they can be prepared by known processes (see Example III-a-1 and H. Bredereck, F. Effenberger, E. Henseleit, Chem. Ber. 1965, 98, 2754; P. Deslongchamps, O. C. Ukken, A. Guida, R. J. Taillefer, Nouv. J. Chim. 1977, 235, 240; R. M. Moriarty, C. L. Yeh, K. C. Ramey, P. W. Whiteburst, J. Am. Chem. Soc. 1970, 21, 6360).

Some of the compounds of the formula (V)

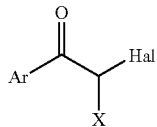

(V)

in which

Ar and Hal are each as defined above and X represents cyano, are known, or they can be prepared by known processes (Gakhar H. K. et. al, J. Indian Chem. Soc. 43 (1971) 953; Corsaro A. Heterocycles 23 (1985) 2645).

The compounds of the formula (VI)

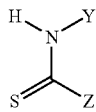

(VI)

in which

Z and Y are each as defined above, are compounds of organic chemistry which are known in principle, and some are commercially available (see also Preparation Example 5).

The compounds of the formula (VIII)

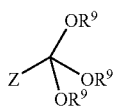

(VIII)

in which

Z and R⁹ are each as defined above, are compounds of organic chemistry which are known in principle, and some of them are commercially available.

Most of the compounds of the formula (IX) are commercially available compounds, or they can be prepared by generally known processes of organic chemistry.

Some of the arylboronic acids of the formula (X) required for carrying out process E are commercially available, or they can be prepared by known processes.

Suitable diluents for process (A) are all organic solvents which are inert towards the reactants. Preference is given to using optionally chlorinated aliphatic or aromatic hydrocarbons, such as toluene, xylene, mesitylene, chlorobenzene, chloroform, methylene chloride, furthermore polar solvents, such as dimethyl sulphoxide, sulpholane, dimethylformamide, dimethylacetamide or N-methylpyrrolidone. It is also possible to use ethers, such as diethyl ether, tetrahydrofuran or dioxane.

Bases suitable for use in process (A) are all customary acid acceptors which do not hydrolyse the reactants.

Preference is given to use tertiary amines, such as triethylamine, pyridine, diazabicyclooctane (DABCO), diazabicycloundecene (DBU), diazabicyclononene (DBN) or N,N-dimethylaniline.

Acids suitable for use in process (A) are all acids which do not hydrolyse the reactants. Preference is given to using organic acids, such as p-toluenesulphonic acid and trifluoroacetic acid.

When carrying out process (A), the reaction temperatures can be varied within a relatively wide range. The process is expediently carried out at temperatures between –20° C. and 160° C., preferably between 0° C. and 120° C.

The process (A) is preferably carried out under atmospheric pressure.

When carrying out process (A), the reaction component of formula (III) is employed in equimolar amounts or in a relatively large excess (up to 5 mol), preferably in 1.5 to 2 times the molar amount, based on the reaction component of the formula (II).

The base which is optionally employed is preferably used in an amount which is equimolar to that of the reaction component of the formula (II). The acid that is employed, if appropriate, is preferably used in catalytic amounts.

The process (B) is characterized in that compounds of the formula (V) are in each case reacted with thioamides of the formula (VI), if appropriate in the presence of a diluent and if appropriate in the presence of an acid binder.

The starting materials of the formula (V) can be prepared by known processes (Gakhar H. K. et al., J. Indian Chem. Soc. 43, (1971), 953 or Corsaro A., Heterocycles 23, (1985), 2645). The compounds of the formula (VI) can be prepared from the corresponding keto compound using thionylating agents, in particular Lawesson's reagent, in inert solvents, such as, for example, toluene (see Preparation Example 5).

Diluents suitable for use in the process (B) according to the invention are all solvents which are inert towards the compounds of the formula (V). Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, and also strongly polar solvents, such as dimethylformamide, N-methylpyrrolidone, dimethyl sulphoxide and sulpholane.

Suitable acid binders for the reaction according to process (B) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, polymeric bases, such as diisopropylaminopolystyrene, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Phosphorus reagents suitable for use in the process (B) according to the invention are alkyl phosphites, such as triethyl phosphite, tributyl phosphite, or triphenylphosphines, such as triphenylphosphine.

The reaction temperature in the process (B) according to the invention can be varied within a relatively wide range. In general, the process is carried out at temperatures between 0° C. and 200° C., preferably between +20° C. and 150° C.

When carrying out the process (B) according to the invention, the starting materials of the formula (V) and the thioamide of the formula (VI) are generally each employed in approximately equivalent amounts. However, it is also possible to use a relatively large excess of one component or the other. Work-up is carried out by customary methods.

The process (C) is characterized in that initially compounds of the formula (II) are condensed with orthoesters of the formula (VIII), and the resulting condensates are, without intermediate characterization, reacted with amines of the formula (IX).

Acid binders suitable for the reaction according to the process (C) according to the invention are, if appropriate, all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, polymeric bases, such as, for example, disopropylaminopolystyrene, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Diluents suitable for the process (C) according to the invention are all solvents which are inert towards the orthoesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic acid esters, such as ethyl acetate, moreover nitrites such as acetonitrile, and also strongly polar solvents, such as dimethylformamide, dimethylacetamide, N-methylpyrrolidone, dimethyl sulphoxide and sulpholane. According to a further process variant, the orthoesters themselves may also be used as solvents. This process variant is emphasized as being preferred.

The reaction temperature in the process (C) according to the invention can be varied within a relatively wide range. In general, the process is carried out at temperatures between −20° C. and 200° C., preferably between 0° C. and 150° C.

The process (C) according to the invention is generally carried out under atmospheric pressure.

When carrying out the process (C) according to the invention, the starting materials of the formula (II) and the appropriate amine of the formula (IX) are generally each employed in approximately equivalent amounts. However, it is also possible to use a relatively large excess (up to 10 mol, preferably up to 3 mol) of one component or the other. The orthoesters of the formula (VIII) are generally employed in a relatively large excess. Work-up is carried out according to customary methods by concentrating the reaction mixture by removing the diluent and excess reactants under reduced pressure and purifying the residue further.

The process (D) is characterized in that compounds of the formula (I) in which Ar, X, Y and Z are each as defined above and K represents oxygen are reacted with sulphurizing agents, if appropriate in the presence of a diluent.

The sulphurizing agents to be used are known chemicals for synthesis, such as, for example, phosphorus pentasulphide or 2,4-bis(4-methoxyphenyl)-1,2,3,4-dithiaphosphetane 2,4-disulphide (Lawesson's reagent).

Diluents suitable for use in the process (D) according to the invention are all solvents which are inert towards the abovementioned reagents. Preference is given to using hydrocarbons, such as benzine, benzene, toluene, xylene and tetralin, furthermore halogenated hydrocarbons, such as methylene chloride, chloroform, chlorobenzene and o-dichlorobenzene, ethers, such as tetrahydrofuran, dioxane, diisopropyl ether or methyl tert-butyl ether.

In the process (D) according to the invention, the reaction temperatures can be varied within a relatively wide range. In general, the process is carried out at temperatures between 0° C. and 250° C., preferably between 40° C. and 200° C.

When carrying out the process (D) according to the invention, the starting materials of the formula (I) and the abovementioned reagents are generally each employed in approximately equivalent amounts. However, it is also possible to use a relatively large excess of up to 5 mol of the abovementioned reagents. Work-up is carried out by customary methods.

Some of the arylboronic acids required for carrying out the process (E), such as, for example, 4-chloro-phenylboronic acid, are commercially available, or they can be prepared by known processes.

Suitable acid acceptors for carrying out the process (E) according to the invention are inorganic or organic bases. These preferably include alkaline earth metal hydroxides, acetates, carbonates or bicarbonates or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicycloundecene (DBU), diazabicyclononene (DBN).

Suitable diluents for carrying out the process (E) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl tert-butyl ether, methyl tert-amyl ether, dioxane, tetra-hydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature in the process (E) according to the invention can be varied within a relatively wide range. In general, the process is carried out at temperatures between 0° C. and +200° C., preferably between 50° C. and +150° C.

When carrying out the process (E) according to the invention, the boronic acid of the formula (X) in which $Ar^{2'}$ is as defined above and compounds of the formula ($I^1$) in which $Ar^1$, K, X, Y, Z and Hal are each as defined above are employed in a molar ratio of from 1:1 to 3:1, preferably from 1:1 to 2:1. The catalyst is generally employed in amounts of from 0.005 to 0.5 mol, preferably from 0.01 to 0.1 mol, per mole of the compound of the formula ($I^1$). The base is generally employed in excess.

The active compounds according to the invention are particularly suitable for use as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The dosages of the active compounds according to the invention required for weed control are between 0.001 and 10 kg/ha, preferably between 0.005 and 5 kg/ha.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

However, the use of the active compounds according to the invention is in no way restricted to these genera, but also extends in the same manner to other plants. With respect to the use of the active compounds according to the invention, particular emphasis is given to the use in connection with transgenic plants since in this case synergistically enhanced activities may be observed.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are highly suitable for the selective control of monocotyledonous weeds in dicotyledonous crops by the pre- and post-emergence method. They can be used very successfully, for example, for the control of harmful grasses in cotton or sugar beet.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are prepared in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral or vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and in addition preferably extenders and/or surfactants.

The active compound according to the invention can be present in its commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia. In preferred embodiments of the present invention, it is also possible to mix safeners with the compounds according to the invention, to increase crop plant compatibility.

Examples of particularly advantageous mixing components are the following:

Fungicides:
aldimorph, ampropylfos, ampropylfos potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemotph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-propyl-1H-1,2,4-triazole-1-ethanol,
α-(2,4-dichlorophenyl)-β-methoxy-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogencarbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxymethanimidamide,
N-formyl-N-hydroxy-DL-alanine sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopren, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin, lambda-cyhalothrin, lufenuron,
malathion, mecarbam, metaldehyde, methamidophos, *Metharhizium anisopliae, Metarhizium flavoviride*, methidathion, methiocarb, methomyl, methoxyfenozide, metolcarb, metoxadiazone, mevinphos, milbemectin, monocrotophos,
naled, nitenpyram, nithiazine, novaluron, nuclear polyhedrosis viruses,
omethoat, oxamyl, oxydemethon M,
*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302,
zeta-cypermethrin, zolaprofos,
(1R-cis)-[5-(phenylmethyl)-3-furanyl]-methyl 3-[(dihydro-2-oxo-3(2H)-furanylidene)-methyl]-2,2-dimethylcyclopropanecarboxylate,
(3-phenoxyphenyl)-methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetlyoxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl[2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl[2-(dipropylamino)-2-oxoethyl]-ethylphosphoramidothioate.

Herbicides:
acetochlor, acifluorfen(-sodium), aclonifen, alachlor, alloxydim(-sodium), ametryne, amidochlor, amidosulflron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfiron(-methyl), ethofumesate, ethoxyfen, ethoxysulfuron, etobenzanid, fenoxaprop(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Furthermore, the active compound according to the invention, in its commercial formulations and in the use forms prepared from these formulations, can be present as a mixture with synergists. Synergists are compounds which increase the activity of the active compounds without it being necessary for the added synergist to be active itself.

The active compound content of the use forms prepared from the commercial formulations can vary within wide ranges. The concentration of active compound in the use forms can be from 0.0000001 to 95% by weight of active compound, preferably between 0.0001 and 1% by weight.

Application is carried out in a customary manner adapted to the use forms.

The active compounds are furthermore suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Blattaria or Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Anoplura, for example, *Phylloxera vastatrix, Pemphigus* spp.,

*Pediculus humanus corporis, Haematopinus* spp. and *Linognathus* spp.

From the order of the Mallophaga, for example, *Trichodectes* spp. and *Damalinea* spp.

From the order of the Thysanoptera, for example, *Frankliniella occidentalis,*

*Hercinothrips femoralis, Thrips palmi* and *Thrips tabaci.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Phylloxera vasturix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp. and *Aulema oryzae.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Liriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemnia* spp. and *Liviomyza* spp.

From the order of the Siphonaptera, for example, *Xenopsylla cheopis* and *Ceratophyllus* spp.

From the order of the Arachnida, for example, *Scorpio maurus* and *Latrodectus mactans.*

From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipulpus* spp.

The phytoparasitic nematodes include, for example, *Pratylenchus* spp. *Radopholus similis, Ditylenchus dipsaci, Tylenchulus semi penetrans, Heteroderma* spp., *Globodera* spp., *Meloidogyne* spp., *Aphelenchoides* spp., *Longidorus* spp., *Xiphinema* spp., *Trichodorus* spp. and *Bursaphelenchus* spp.

The active compounds according to the invention have high insecticidal and acaricidal activity after foliar and soil application.

At certain concentrations or application rates, the compounds according to the invention also have fungicidal action. Furthermore, they can also be used as microbicides or antimycotics.

When used against hygiene pests and pests of stored products, the active compound has excellent residual activity on wood and clay, and good stability to alkali on limed substrates.

The active compounds according to the invention act not only against plant, hygiene and stored-product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Caalliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100- to 10 000-fold dilution, or they can be used as a chemical bath.

It has furthermore been found that the compounds of the formula (I) according to the invention also have a strong insecticidal action against insects which destroy industrial materials.

The following insects may be mentioned as examples and as preferred—but without a limitation:

Beetles, such as *Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus.*

Hymenopterons, such as *Sirex juvencus, Urocerus gigas, Urocerus gigas taignus* and *Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccarina.*

Industrial materials in the present connection are to be understood as meaning non-living materials, such as, preferably, plastics, adhesives, sizes, papers and cardboards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the protection of wood and timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be protected.

Solvents and/or diluents which are used are an organochemical solvent or solvent mixture and/or an oily or oil-like organochemical solvent or solvent mixture of low volatility and/or a polar organochemical solvent or solvent mixture and/or water, and if appropriate an emulsifier and/or wetting agent.

Organochemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organochemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organochemical solvent or solvent mixture is replaced by an aliphatic polar organochemical solvent or solvent mixture. Aliphatic organochemical solvents containing hydroxyl and/or ester and/or ether groups, such as, for example, glycol ethers, esters or the like, are preferably used.

Organochemical binders which are used in the context of the present invention are the synthetic resins and/or binding drying oils which are known per se, are water-dilutable and/or are soluble or dispersible or emulsifiable in the organochemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organochemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organochemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compounds according to the invention can be used particularly effectively for controlling plant-damaging insects, such as, for example, against the larvae of the mustard beetle (*Phaedon cochleariae*), against the larvae of the green rice leafhopper (*Nephotettix cincticeps*) and against the larvae of the green peach aphid (*Myzus persicae*).

In addition to the acaricidal, herbicidal and insecticidal properties described, a fungicidal activity of the active compounds according to the invention is noticeable. In both 'in vitro' and 'in vivo' studies, a broad fungicidal effect can be observed.

Moreover, it was noticed that the active compounds are, in particular, also suitable for controlling mildew, leaf blotch and *Fusaria* on the infected plants.

The preparation and the use of the active compounds according to the invention is shown in the examples below.

PREPARATION EXAMPLES

Example 1

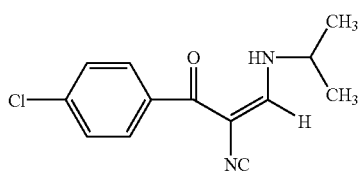

Comp. No. I-a-1

(Process C)

At 60° C., a mixture of 0.9 g of 4-chlorobenzoylacetonitrile and trimethyl formate is admixed with 0.3 g of isopropylamine. The reaction mixture is heated at 125–130° C., and the reaction is monitored by thin-layer chromatography.

After all of the starting material has been converted, the reaction mixture is concentrated using a rotary evaporator, and the product that has been formed is extracted using methylene chloride/NaHCO₃ solution.

The compounds contained in the solution were separated by column chromatography on a silica gel phase using the mobile phase hexane/ethyl acetate (2:1).

One of the main fractions gave, after evaporation of the solvent, 0.65 g (yield 55% of theory) of 2-(4-chlorobenzoyl)-3-(N-methylamino)-propenonitrile of melting point 148° C.

Example 2

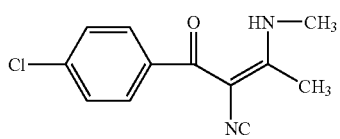

Comp. N. I-a-59

(Process A)

A mixture of 0.7 g of 4-chloro-benzoylacetonitrile, 0.5 g of methyl N-methyliminoacetate and 8 ml of toluene is initially charged and heated at 80° C. The reaction mixture is stirred at 80° C. for 10 hours and then concentrated by evaporating the solvent, and the precipitated solid is recrystallized from methyl t-butyl ether/dichloromethane.

This gives 0.51 g (yield 54.9% of theory) of 2-(4-chlorobenzoyl)-3-(N-methylamino)-crotononitrile of melting point 152° C.

Example 3

Comp. No. I-a-41

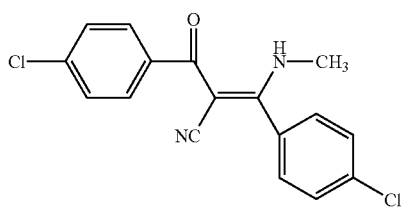

(Process A)

1 g of thiomethyl N-methyl-4-chloroiminobenzoate and 1 g of 4-chlorobenzoylacetonitrile are added to 10 ml of toluene. The mixture is stirred for 4 hours. After complete conversion (TLC), the components contained in the mixture are separated by column chromatography on a silica gel phase using the mobile phase hexane/ethyl acetate (2:1).

One of the main fractions gave, after evaporation of the solvent, 1.30 g (yield 81% of theory) of 2-(4-chlorobenzoyl)-3-(4-chlorophenyl)-3-(N-methylamino)-propenonitrile of melting point 182° C.

Example 4

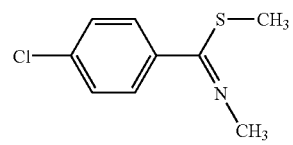

Comp. No. III-a-1

At 0° C., 5 g of N-methyl-4-chloro-thiobenzamide are dissolved in acetonitrile and admixed with 3.3 g of potassium hydroxide. At a temperature of 20° C., 4 g of methyl iodide are added, and the mixture is then heated at 60° C. After complete conversion (TLC), the reaction mixture is filtered and concentrated by evaporation of the solvent using a rotary evaporator.

This gave 2.0 g (yield 40% of theory) of thiomethyl N-methyl-4-chloroiminobenzoate, which decomposes readily.

Example 5

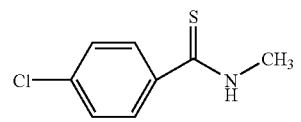

Comp No. VI-a-1

At 0° C., 80 g of the compound N-methyl-4-chlorobenzamide in 600 ml of pyridine are admixed with 107 g of phosphorus pentasulphide. The mixture is heated to 80° C. and then kept at this temperature for 2 hours.

The components contained in the mixture were separated by column chromatography on a silica gel phase using the mobile phase hexane/ethyl acetate (10:1).

One of the main fractions gave, after evaporation of the solvent, 46 g of N-methyl-4-chloro-thiobenzamide (yield 52% of theory).

Example 6

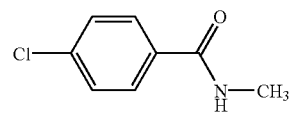

At −30° C., about 200 ml of methylamine are condensed into 400 ml of THF. At from −10° C. to 0° C., the reaction solution is then admixed with 75 g of 4-chlorobenzoyl chloride (as a solution in 30 ml of THF). At 20° C., the further progress of the reaction is monitored by thin-layer chromatography.

After complete conversion, the compounds contained in the mixture are separated by column chromatography on a silica gel phase using the mobile phase hexane/ethyl acetate (2:1).

The main fraction gave, after evaporation of the solvent, 80 g (yield 99% of theory) of N-methyl-4-chloro-benzamide.

Example 7

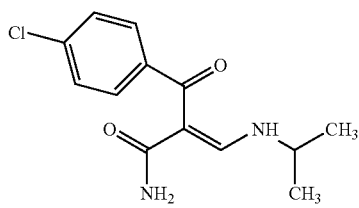

Comp. N. I-a-60

1 g of 4-chlorobenzoyl-acetamide (known from JP-A 89-108491) and 10 ml of trimethyl orthoformate are mixed and reacted at 90° C. for one hour. After cooling to 60° C., 2 ml of i-propylamine are added. The mixture is then heated at 110° C. for 10 minutes. After complete conversion, the compounds contained in the mixture are separated by column chromatography on a silica gel phase using the mobile phase hexane/ethyl acetate (2:1).

The main fraction gave, after evaporation of the solvent, 0.2 g (yield 7.5% of theory) of 2-(4-chlorobenzoyl)-3-(N-isopropylamino)-propenamide.

$^1$H-NMR (400 MHz, $d_6$-DMSO): δ=1.14 (d, 6H, CH(C$\underline{H}_3$)$_2$), 3.58 (m, 1H, C$\underline{H}$(CH$_3$)$_2$), 7.16 (d, br, 1H, CONH), 8.86 (d, br, 1H, CONH), 10.83 (br, 1H, NH) ppm, UV (acetonitrile/H$_3$PO$_4$ buffer gradient): $\lambda_{max}$ 244, 292 nm.

Example 8

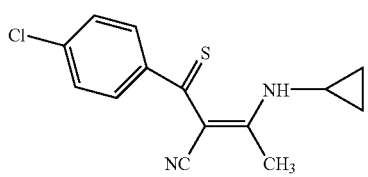

Comp. N. I-a-61

(Process D)

At a temperature of 20° C., 0.8 g of 2-(4-chlorobenzoyl)-3-(N-cyclopropylamino)-crotononitrile is admixed with 0.7 g of Lawesson's reagent and reacted for one hour. After complete conversion, the components contained in the mixture are separated by column chromatography on a silica gel phase using the mobile phase hexane/ethyl acetate (2:1).

The main fraction gave, after evaporation of the solvent, 0.7 g (yield 84% of theory) of 2-[(4-chlorophenyl)-thiocarbonyl]-3-(N-cyclopropylamino)-crotononitrile of melting point 215° C.

Example 9

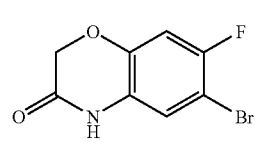

Comp. No. (XV)'-1

30.0 g of 6-fluoro-4H-benz[1,4]oxazin-3-one are initially charged in 300 ml of dichloromethane, and 37.4 g of bromine are then slowly added dropwise at room temperature. The mixture is heated at 30° C. with stirring for 15 h. The reaction solution is cooled to room temperature and poured onto ice. The aqueous phase is extracted repeatedly with dichloromethane. The combined organic phases are washed with saturated sodium thiosulphate solution, dried over magnesium sulphate and concentrated. This give 44.1 g (yield 99.5% of theory) of 7-bromo-6-fluoro-4H-benz[1,4]oxazin-3-one of melting point 244° C.

Example 10

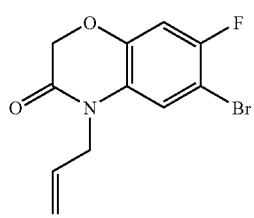

Comp. No. (XV-1)

Under argon, 25.5 g of 7-bromo-6-fluoro-4H-benz[1,4]oxazin-3-one are initially charged in 120 ml of DMF and, at 0° C., admixed a little at a time with 28.0 g of potassium carbonate. At 0° C., 13.0 ml of allyl bromide are then added dropwise, and the mixture is stirred at room temperature for 15 h. The mixture is poured into 1200 ml of ice-water and extracted repeatedly with ethyl acetate, and the combined organic phases are washed with saturated aqueous sodium chloride solution, dried over magnesium sulphate and concentrated.

The crude product is purified by silica gel column chromatography (mobile phase: ethyl acetate/cyclohexane 1:1), giving 23.8 g (yield 81.9% of theory) of N-allyl-7-bromo-6-fluoro-4H-benz[1,4]oxazin-3-one of melting point 92° C.

Example 11

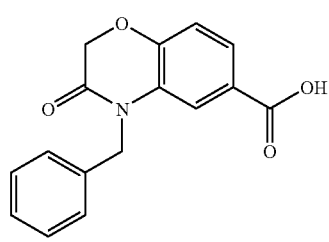

Comp. No. (XIV-b-2)

20.0 g of N-benzyl-7-methoxycarbonyl-4H-benz[1,4]oxazin-3-one are initially charged in 750 ml of MeOH. At room temperature, 35 ml of 2N aqueous sodium hydroxide solution are added dropwise, and the mixture is stirred at 40–55° C. for 30 h. The reaction solution is cooled to room temperature and poured into a mixture of 200 ml of 1N HCl and 1 kg of ice. The crude product is filtered off with suction, washed with water and dried. This gives 18.2 g (yield 95.5% of theory) of N-benzyl-7-hydroxycarbonyl-4H-benz[1,4]oxazin-3-one of melting point 230° C.

The following compounds are obtained analogously to the preparation examples and in accordance with the general statements on the preparation of compounds of the formula (I):

TABLE 1

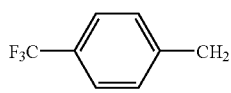

(I-a)

| Comp. No. | $G_n$ | Y | Z | m.p. ° C. |
|---|---|---|---|---|
| I-a-1 | 4-Cl | i-$C_3H_7$ | H | 148 |
| I-a-2 | 4-Cl |  | H | 119 |
| I-a-3 | 3,5-$(CF_3)_2$ | $C_2H_5$ | H | 78–80 |
| I-a-4 | 3,5-$(CF_3)_2$ | $CH_3$ | H | 150 |
| I-a-5 | 3,5-$(CF_3)_2$ | H | H | 149 |
| I-a-7 | 4-Cl | $CH_3$ | H | 208 |
| I-a-8 | 4-Cl | 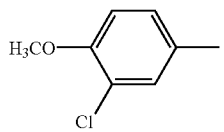 | H | 138 |
| I-a-9 | 3,5-$(CF_3)_2$ | 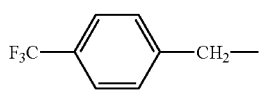 | H | 110 |
| I-a-10 | 4-Cl | $F_3C$—$CH_2$— | H | 155 |
| I-a-11 | 3,5-$(CF_3)_2$ | $F_3C$—$CH_2$— | H | 154 |
| I-a-12 | 3,5-$(CF_3)_2$ | i-$C_3H_7$ | H | 134 |
| I-a-13 | 4-Cl |  | $CH_3$ | 58–60 |
| I-a-14 | 4-Cl | i-$C_3H_7$ | $CH_3$ | 137 |
| I-a-15 | 3,5-$(CF_3)_2$ | i-$C_3H_7$ | $CH_3$ | 118–120 |
| I-a-16 | 3,5-$(CF_3)_2$ | $C_2H_5$ | $CH_3$ | oil |
| I-a-17 | 3,5-$(CF_3)_2$ | $CH_3$ | $CH_3$ | oil |
| I-a-18 | 3,5-$(CF_3)_2$ | H | $CH_3$ | 172–174 |
| I-a-19 | 4-Cl | H | $CH_3$ | 162 |
| I-a-20 | 4-Cl | $CH_3$ | $CH_3$ | 171 |
| I-a-21 | 4-Cl | $F_3C$—$CH_2$ | $CH_3$ | 145 |
| I-a-22 | 3,5-$(CF_3)_2$ | $F_3C$—$CH_2$ | $CH_3$ | 122 |
| I-a-23 | 4-Cl |  | $CH_3$ | 82–84 |
| I-a-24 | 3,5-$(CF_3)_2$ |  | $CH_3$ | 78–80 |
| I-a-25 | 4-Cl | i-$C_3H_7$ | $C_2H_5$ | 162 |
| I-a-26 | 3,5-$(CF_3)_2$ | $C_2H_5$ | $C_2H_5$ | 105 |
| I-a-27 | 4-Cl | $CH_3$ | $C_2H_5$ | 149 |
| I-a-28 | 3,5-$(CF_3)_2$ | i-$C_3H_7$ | n-$C_3H_7$ | 83 |
| I-a-29 | 4-Cl | i-$C_3H_7$ | n-$C_3H_7$ | 102 |
| I-a-30 | 3,5-$(CF_3)_2$ | $CH_3$ | n-$C_3H_7$ | oil |
| I-a-31 | 3,5-$(CF_3)_2$ | $C_2H_5$ | n-$C_3H_7$ | oil |
| I-a-32 | 3,5-$(CF_3)_2$ | i-$C_3H_7$ | n-$C_4H_9$ | 73 |

TABLE 1-continued (I-a)

| Comp. No. | $G_n$ | Y | Z | m.p. °C. |
|---|---|---|---|---|
| I-a-33 | 3,5-$(CF_3)_2$ | $C_2H_5$ | n-$C_4H_9$ | oil |
| I-a-34 | 3,5-$(CF_3)_2$ | $CH_3$ | n-$C_4H_9$ | oil |
| I-a-35 | 4-Cl | i-$C_3H_7$ | n-$C_4H_9$ | 60 |
| I-a-36 | 4-Cl | H | 4-Cl-C6H4 | 270 |
| I-a-37 | 4-Cl | H | C6H5 | 242 |
| I-a-38 | 4-Cl | i-$C_3H_7$ | 4-Cl-C6H4 | 144 |
| I-a-39 | 3,5-$(CF_3)_2$ | H | 4-Cl-C6H4 | 146 |
| I-a-40 | 3,5-$(CF_3)_2$ | H | C6H5 | 182 |
| I-a-42 | 3,5-$(CF_3)_2$ | $CH_3$ | 4-Cl-C6H4 | 170 |
| I-a-43 | 4-Cl | i-$C_3H_7$ | 3,4-Cl2-C6H3 | 150 |
| I-a-44 | 4-Cl | i-$C_3H_7$ | C6H5 | 146–148 |
| I-a-45 | 4-Cl | $C_2H_5$ | 4-Cl-C6H4 | 135 |
| I-a-46 | 3,5-$(CF_3)_2$ | $C_2H_5$ | 4-Cl-C6H4 | 132–134 |
| I-a-47 | 3,5-$(CF_3)_2$ | i-$C_3H_7$ | 3,4-Cl2-C6H3 | 138–140 |
| I-a-48 | 3,5-$(CF_3)_2$ | i-$C_3H_7$ | C6H5 | 152 |

TABLE 1-continued (I-a)

[Structure: phenyl(Gn)-C(=O)-C(CN)=C(Z)-NH-Y]

| Comp. No. | Gn | Y | Z | m.p. °C. |
|---|---|---|---|---|
| I-a-49 | 3,5-(CF$_3$)$_2$ | C$_2$H$_5$ | phenyl | 182 |
| I-a-50 | 3,5-(CF$_3$)$_2$ | CH$_3$ | phenyl | 173 |
| I-a-51 | 3,5-(CF$_3$)$_2$ | C$_2$H$_5$ | 3,4-Cl$_2$-phenyl | 147 |
| I-a-52 | 3,5-(CF$_3$)$_2$ | CH$_3$ | 3,4-Cl$_2$-phenyl | 139 |
| I-a-53 | 4-Cl | C$_2$H$_5$ | phenyl | 133 |
| I-a-54 | 3,5-(CF$_3$)$_2$ | i-C$_3$H$_7$ | 4-OCH$_3$-3-Cl-phenyl | 136–138 |
| I-a-55 | 3,5-(CF$_3$)$_2$ | C$_2$H$_5$ | 4-OCH$_3$-3-Cl-phenyl | 138 |
| I-a-56 | 3,5-(CF$_3$)$_2$ | CH$_3$ | 4-OCH$_3$-3-Cl-phenyl | 148 |
| I-a-57 | 4-Cl | i-C$_3$H$_7$ | 4-OCH$_3$-3-Cl-phenyl | oil |
| I-a-58 | 2,4-F$_2$ | CH$_3$ | CH$_3$ | 146 |
| I-a-59 | 4-Cl | CH$_3$ | CH$_3$ | 152 |
| I-a-60 | 4-Cl | i-C$_3$H$_7$ | H | |
| I-a-61 | 3,5-(CF$_3$)$_2$ | CH(CH$_3$)$_2$ | C$_2$H$_5$ | 123 |
| I-a-62 | 4-Cl | CH(CH$_3$)$_2$ | 4-Cl-phenylethyl | oil |

TABLE 1-continued (I-a)

| Comp. No. | $G_n$ | Y | Z | m.p. °C. |
|---|---|---|---|---|
| I-a-63 | 4-Cl | CH₂-cyclopropyl | CH₃ | 113 |
| I-a-64 | 2-F, 4-Cl, 5-O-allyl | cyclopropyl | CH₃ | 83 |
| I-a-65 | 4-Cl | CH₂-(2-pyridyl) | CH₃ | 124 |
| I-a-66 | 4-Cl | n-C₃H₇ | CH₃ | 134 |
| I-a-67 | 4-Cl | CH₂CH(CH₃)₂ | CH₃ | 120 |
| I-a-68 | 4-Cl | C(CH₃)₃ | CH₃ | 123 |
| I-a-69 | 4-Cl | CH₂C(CH₃)₃ | CH₃ | 147 |
| I-a-70 | 4-Cl | (R)-CH(CH₃)Ph | CH₃ | oil |
| I-a-71 | 4-Cl | CH₂-(4-pyridyl) | CH₃ | oil |
| I-a-72 | 4-Cl | CH₂CH₂-(4-MeO-C₆H₄) | CH₃ | 134 |
| I-a-73 | 3,5-(CF₃)₂ | CH₂CH(CH₃)C₂H₅ | CH₃ | oil |
| I-a-74 | 4-Cl | cyclo-C₅H₉ | CH₃ | 98 |
| I-a-75 | 4-Cl | CH₂CH(CH₃)C₂H₅ | CH₃ | oil |
| I-a-76 | 4-Cl | C(CH₃)₂CH₂C(CH₃)₃ | CH₃ | 99 |
| I-a-77 | 4-Cl | C(CH₃)₂(CN) | CH₃ | 143 |
| I-a-78 | 4-Cl | C(C₂H₅)₂C≡CH | CH₃ | oil |
| I-a-79 | 4-Cl | C(CH₃)₂C≡CH | CH₃ | 95 |
| I-a-80 | 4-Cl | C(CH₃)₂C₂H₅ | CH₃ | oil |
| I-a-81 | 4-Cl | CH₂-cyclopropyl | H | 124 |
| I-a-82 | 3,5-(CF₃)₂ | CH₂CH=CH₂ | H | 99 |
| I-a-83 | 2-F, 4-Cl, 5-O-allyl | CH(CH₃)₂ | H | oil |
| I-a-84 | 2-F, 4-Cl, 5-O-allyl | cyclopropyl | H | 143 |
| I-a-85 | 2-F, 4-Cl, 5-O-allyl | CH₃ | H | 162 |
| I-a-86 | 2-F, 4-CN, 5-O-benzyl | CH₃ | H | 158 |

TABLE 1-continued
(I-a)
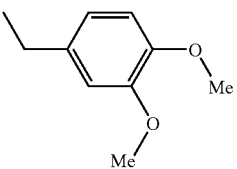
| Comp. No. | $G_n$ | Y | Z | m.p. ° C. |
|---|---|---|---|---|
| I-a-87 | 4-Cl | 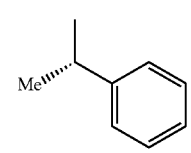 | H | 133 |
| I-a-88 | 4-Cl | n-$C_3H_7$ | H | 108 |
| I-a-89 | 4-Cl | $CH_2CH(CH_3)_2$ | H | 123 |
| I-a-90 | 4-Cl | $C(CH_3)_3$ | H | 125 |
| I-a-91 | 4-Cl | $CH_2C(CH_3)_3$ | H | 121 |
| I-a-92 | 4-Cl | 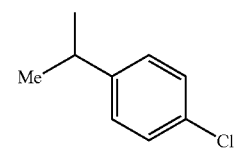 | H | oil |
| I-a-93 | 4-Cl | 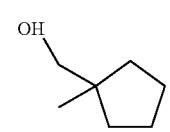 | H | oil |
| I-a-94 | 3,5-$(CF_3)_2$ | $CH(CH_3)C_2H_5$ | H | 146 |
| I-a-95 | 4-Cl | $C(CH_3)_2CH_2OH$ | $CH_3$ | oil |
| I-a-96 | 4-Cl | $C(CH_3)_2CH(CH_3)CH_2OH$ | $CH_3$ | 181 |
| I-a-97 | 4-Cl | $C(C_3H_6OH)_3$ | $CH_3$ | oil |
| I-a-98 | 4-Cl | 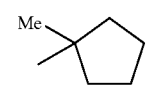 | $CH_3$ | oil |
| I-a-99 | 4-Cl | 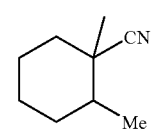 | $CH_3$ | oil |
| I-a-100 | 4-Cl | 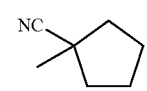 | $CH_3$ | oil |
| I-a-101 | 4-Cl | 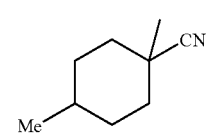 | $CH_3$ | wax |
| I-a-102 | 4-Cl |  | $CH_3$ | wax |

TABLE 1-continued (I-a)

| Comp. No. | G_n | Y | Z | m.p. ° C. |
|---|---|---|---|---|
| I-a-103 | 4-Cl | 4-cyano-4-methyl-tetrahydropyran | CH$_3$ | 191 |
| I-a-104 | 4-Cl | 1-cyano-1-methyl-cyclohexyl | CH$_3$ | wax |
| I-a-105 | 4-Cl | 1-benzyl-3-methyl-piperidin-3-yl | CH$_3$ | oil |
| I-a-106 | 4-Cl | 1-benzyl-4-methyl-piperidin-4-yl | CH$_3$ | oil |
| I-a-107 | 4-Cl | 2-phenyl-prop-2-yl | CH$_3$ | 105 |
| I-a-108 | 4-Cl | 2-(4-chlorophenyl)-2-cyano-prop-2-yl | CH$_3$ | oil |
| I-a-109 | 4-Cl | 1-(4-chlorophenyl)-2-methyl-prop-2-yl | CH$_3$ | oil |

TABLE 1-continued
(I-a)
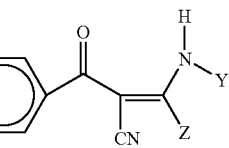
| Comp. No. | G$_n$ | Y | Z | m.p. ° C. |
|---|---|---|---|---|
| I-a-110 | 4-Cl | 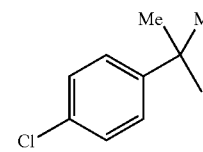 | CH$_3$ | 199 |
| I-a-111 | 4-Cl | 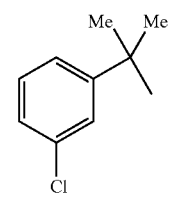 | CH$_3$ | 121 |
| I-a-112 | 4-Cl | 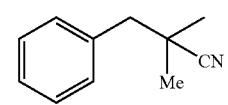 | CH$_3$ | 193 |
| I-a-113 | 4-Cl | 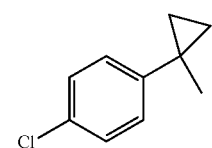 | CH$_3$ | oil |
| I-a-114 | 4-Cl | 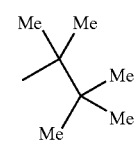 | CH$_3$ | oil |
| I-a-115 | 4-Cl | 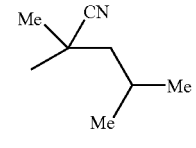 | CH$_3$ | 119 |
| I-a-116 | 4-Cl | 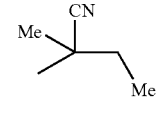 | CH$_3$ | wax |
| I-a-117 | 4-Cl | 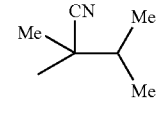 | CH$_3$ | oil |
| I-a-118 | 4-Cl |  | CH$_3$ | oil |

TABLE 1-continued
(I-a)
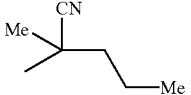
| Comp. No. | $G_n$ | Y | Z | m.p. °C. |
|---|---|---|---|---|
| I-a-119 | 4-Cl | 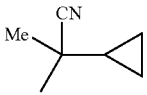 | $CH_3$ | oil |
| I-a-120 | 4-Cl | 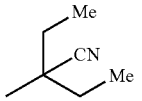 | $CH_3$ | wax |
| I-a-121 | 4-Cl | 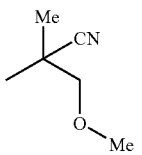 | $CH_3$ | 146 |
| I-a-122 | 4-Cl | 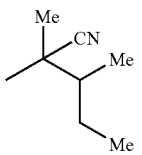 | $CH_3$ | 99 |
| I-a-123 | 4-Cl | 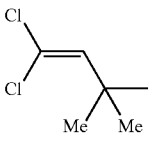 | $CH_3$ | oil |
| I-a-124 | 4-Cl | 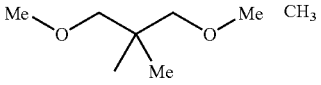 | $CH_3$ | oil |
| I-a-125 | 4-Cl | $C(CH_3)(CH_2F)_2$ | $CH_3$ | 114 |
| I-a-126 | 4-Cl | $C(CH_3)_2CH_2F$ | $CH_3$ | 106 |
| I-a-127 | 4-Cl | $C(CH_3)_2CF_3$ | $CH_3$ | wax |
| I-a-128 | 4-Cl | $C(CH_2F)_3$ | $CH_3$ | oil |
| I-a-129 | 4-Cl | $C(CHF_2)_3$ | $CH_3$ | oil |
| I-a-130 | 4-Cl | 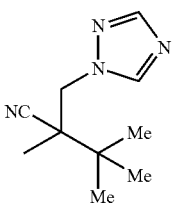 | $CH_3$ | 101 |
| I-a-131 | 4-Cl | 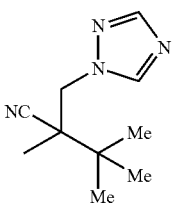 | $CH_3$ | oil |

TABLE 1-continued
(I-a)
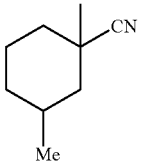
| Comp. No. | $G_n$ | Y | Z | m.p. ° C. |
|---|---|---|---|---|
| I-a-132 | 4-Cl | 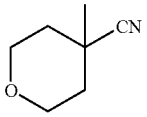 | $CH_3$ | wax |
| I-a-133 | 4-Cl | 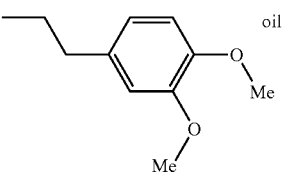 | $CH_3$ | oil |
| I-a-134 | 2-F, 4-Cl, 5-O-allyl | $C(CH_3)_3$ | $CH_3$ | 119 |
| I-a-135 | 3,5-$(CF_3)_2$ | $CH_3$ | 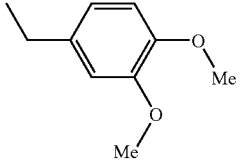 | oil |
| I-a-136 | 4-Cl | 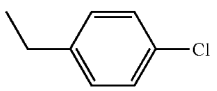 | $CH_3$ | 140 |
| I-a-137 | 4-Cl | 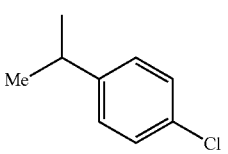 | $CH_3$ | 115 |
| I-a-138 | 4-Cl | 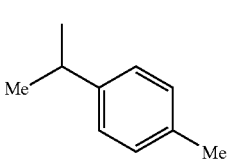 | $CH_3$ | oil |
| I-a-139 | 4-Cl | 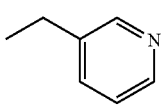 | $CH_3$ | oil |
| I-a-140 | 4-Cl |  | $CH_3$ | oil |

TABLE 1-continued (I-a)

| Comp. No. | $G_n$ | Y | Z | m.p. ° C. |
|---|---|---|---|---|
| I-a-141 | 3,5-(CF$_3$)$_2$ | 3,4-dimethoxyphenethyl | CH$_3$ | oil |
| I-a-142 | 3,5-(CF$_3$)$_2$ | CH$_2$CH(CH$_3$)$_2$ | CH$_3$ | oil |
| I-a-143 | 3,5-(CF$_3$)$_2$ | C(CH$_3$)$_3$ | CH$_3$ | oil |
| I-a-144 | 3,5-(CF$_3$)$_2$ | CH$_2$C(CH$_3$)$_3$ | CH$_3$ | oil |
| I-a-145 | 3,5-(CF$_3$)$_2$ | (R)-1-phenylethyl | CH$_3$ | oil |
| I-a-146 | 3,5-(CF$_3$)$_2$ | 1-(4-chlorophenyl)ethyl | CH$_3$ | oil |
| I-a-147 | 3,5-(CF$_3$)$_2$ | 1-(4-methylphenyl)ethyl | CH$_3$ | oil |
| I-a-148 | 3,5-(CF$_3$)$_2$ | 2-(pyridin-3-yl)ethyl | CH$_3$ | oil |
| I-a-149 | 3,5-(CF$_3$)$_2$ | 2-(pyridin-4-yl)ethyl | CH$_3$ | oil |
| I-a-150 | 3,5-(CF$_3$)$_2$ | 4-methoxyphenethyl | CH$_3$ | oil |
| I-a-151 | 3,5-(CF$_3$)$_2$ | cyclo-C$_5$H$_9$ | CH$_3$ | oil |
| I-a-152 | 3,5-(CF$_3$)$_2$ | n-C$_3$H$_7$ | CH$_3$ | oil |
| I-a-153 | 3,5-(CF$_3$)$_2$ | 3,4-dimethoxyphenethyl | CH$_3$ | oil |

TABLE 1-continued (I-a)

[Structure: phenyl ring with G_n substituent, connected to C(=O)-C(CN)=C(Z)-NH-Y]

| Comp. No. | G_n | Y | Z | m.p. °C. |
|---|---|---|---|---|
| I-a-154 | 4-Cl | [CH₂CH₂-(3,4-dimethoxyphenyl)] | H | 131 |
| I-a-155 | 4-Cl | [CH₂-(4-Me, α-Me phenyl)] | H | oil |
| I-a-156 | 4-Cl | [CH₂CH₂-(4-methoxyphenyl)] | H | — |
| I-a-157 | 4-Cl | CH₂CH(CH₃)C₂H₅ | H | 84 |
| I-a-158 | 3,5-(CF₃)₂ | [CH₂-(2-pyridyl)] | H | 131 |
| I-a-159 | 3,5-(CF₃)₂ | cyclo-C₆H₁₁ | H | 158 |
| I-a-160 | 3,5-(CF₃)₂ | [CH₂-(3,4-dimethoxyphenyl)] | H | 124 |
| I-a-161 | 3,5-(CF₃)₂ | [CH₂CH₂-(3,4-dimethoxyphenyl)] | H | 149 |
| I-a-162 | 3,5-(CF₃)₂ | n-C₃H₇ | H | 119 |
| I-a-163 | 3,5-(CF₃)₂ | CH₂CH(CH₃)₂ | H | 144 |

TABLE 1-continued (I-a)

| Comp. No. | $G_n$ | Y | Z | m.p. °C. |
|---|---|---|---|---|
| I-a-164 | 3,5-$(CF_3)_2$ | $C(CH_3)_3$ | H | 123 |
| I-a-165 | 3,5-$(CF_3)_2$ | $CH_2C(CH_3)_3$ | H | 139 |
| I-a-166 | 3,5-$(CF_3)_2$ | (S)-1-phenylethyl (Me, Ph) | H | oil |
| I-a-167 | 3,5-$(CF_3)_2$ | 1-(4-chlorophenyl)ethyl | H | oil |
| I-a-168 | 3,5-$(CF_3)_2$ | 1-(4-methylphenyl)ethyl | H | 95 |
| I-a-169 | 3,5-$(CF_3)_2$ | 2-pyridylmethyl | H | 102 |
| I-a-170 | 3,5-$(CF_3)_2$ | 4-pyridylmethyl | H | oil |
| I-a-171 | 3,5-$(CF_3)_2$ | 2-(4-methoxyphenyl)ethyl | H | 134 |
| I-a-172 | 3,5-$(CF_3)_2$ | $CH_2CH(CH_3)C_2H_5$ | H | 119 |

In the Tables, "Me" denotes a methyl group ($CH_3$).

The following compound is obtained analogously to the preparation examples and in accordance with the general statements on the preparation of compounds of formula (I) in the description:

TABLE 2

(I-b)

| Comp. No. | Y | Z | m.p. ° C. |
|---|---|---|---|
| I-b-1 | C(CH$_3$)$_3$ | CH$_3$ | oil |

The following compounds are obtained analogously to Preparation Example 4 and in accordance with the general statements on the preparation of compounds of the formula (III):

(III-a)

| Comp. N. | R$^8$ | Y | Rg | m.p. ° C. |
|---|---|---|---|---|
| III-a-1 | CH$_3$ | CH$_3$ | 4-Cl | oil |
| III-a-2 | CH$_3$ | allyl | H | oil |
| III-a-3 | CH$_3$ | allyl | 4-Cl | oil |
| III-a-4 | CH$_3$ | i-C$_3$H$_7$ | 4-Cl | oil |
| III-a-5 | CH$_3$ | C$_2$H$_5$ | 4-Cl | oil |
| III-a-6 | CH$_3$ | CH$_2$—CF$_3$ | 4-Cl | oil |

The following compounds are obtained analogously to Preparation Example 5 and in accordance with the general statements on the preparation of compounds of the formula (VI):

(VI-a-1)

| Comp. No. | Y | Rg |
|---|---|---|
| VI-a-1 | CH$_3$ | 4-Cl |
| VI-a-2 | i-C$_3$H$_7$ | 4-Cl |
| VI-a-3 | allyl | 4-Cl |
| VI-a-4 | C$_2$H$_5$ | 4-Cl |
| VI-a-5 | CH$_2$—CF$_3$ | 4-Cl |

Example

Post-emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. After 3 weeks, the degree of damage to the plants is rated in % damage in comparison to the development of the untreated control.

The figures denote:

| 0% = | no effect (like untreated control) |
| 100% = | total destruction |

In this test, for example, the compounds of Preparation Examples I-a-35, I-a-20, I-a-4, I-a-17, I-a-3, I-a-59, I-a-58, I-a-29, I-a-8 and I-a-23 exhibit strong activity against weeds, and some are tolerated well by crop plants, such as, for example, wheat.

Example

Pre-emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. The amount of water per unit area is advantageously kept constant. The concentration of active compound in the preparation is immaterial, only the application rate of active compound per unit area matters. After three weeks, the degree of damage to the plants is rated in % damage in comparison to the development of the untreated control.

The figures denote:

| 0% = | no effect (like untreated control) |
| 100% = | total destruction |

In this test, for example, the compounds of Preparation Examples I-a-3, I-a-17, I-a-20, I-a-4, I-a-58, I-a-59, I-a-23, I-a-8 and I-a-21 exhibit strong activity against weeds, and some are tolerated well by crop plants, such as, for example, wheat and soya.

Example A

*Meloidogyne* Test

| Solvent: | 30 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action is determined in % using gall formation as a measure. 100% means that no galls were found; 0% means that the number of galls on the treated plants corresponds to that on the untreated control.

In this test, for example, the following compounds of the preparation examples exhibit good activity:

I-a-39, I-a-42, I-a-5

Example B

*Phaedon* Larvae Test

| Solvent: | 30 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the preparation examples show good activity:

I-a-13, I-a-49, I-a-44, I-a-15, I-a-19, I-a-53

Example C

*Plutella* Test

| Solvent: | 30 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the owlet moth (*Plutella xylostella*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

I-a-58, I-a-45

Example D

*Spodoptera frugiperda* Test

| Solvent: | 30 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

I-a-42, I-a-45, I-a-48, I-a-18, I-a-52

Example E

*Tetranychus* Test (OP-Resistant/Dip Treatment)

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, for example, the following compounds of the preparation examples show good activity:

I-a-3

The invention claimed is:

1. A process for preparing a compound of formula (I), $$\underset{Ar}{\overset{K}{\|}}C-\underset{X}{\overset{}{C}}=\underset{Z}{\overset{H}{C}}-\underset{}{\overset{H}{N}}-Y, \quad (I)$$

wherein
K represents oxygen or sulphur,
Ar represents Ar$^1$, where Ar$^1$ represents phenyl which is mono- to trisubstituted by chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, trifluoromethyl, difluoromethoxy, trifluoromethoxy, methylenedioxy, tetrafluoroethylenedioxy, difluoromethylthio, trifluoromethylthio, trifluoromethylsulphinyl, trifluoromethylsulphonyl, benzyloxy, hydroxyl, mercapto, cyano or amino,
or represents Ar$^2$, where Ar$^2$ represents Ar$^1$ which is additionally substituted by phenyl or phenoxy, where these substituents are for their part mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano,
X represents —CN, —CO—NH$_2$, or $$-\overset{S}{\underset{NH_2,}{\overset{\|}{C}}}$$

Y represents hydrogen, in each case optionally mono- or poly-hydroxy-substituted C$_1$–C$_6$-alkyl, C$_1$–C$_4$-halogenoalkyl, C$_3$–C$_4$-alkenyl, C$_3$–C$_6$-alkinyl, C$_1$–C$_4$-alkoxy-C$_2$–C$_3$-alkyl, di-C$_1$–C$_2$-alkoxy-C$_2$–C$_4$-alkyl, C$_1$–C$_2$-alkoxy-C$_2$–C$_4$-cyanoalkyl, C$_1$–C$_2$-alkylthio-C$_2$–C$_3$-alkyl, C$_1$–C$_5$-halogenoalkenyl or C$_1$–C$_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted C$_3$–C$_6$-cycloalkyl or C$_3$–C$_6$-cycloalkyl-C$_1$–C$_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro,
Z represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro,
wherein the process comprises:

(A) if K represents oxygen,
a compound of the formula (II)

$$\underset{Ar}{\overset{O}{\|}}C-\overset{}{C}H_2-X \quad (II)$$

is reacted with a compound of the formula (III)

$$R^8-W-\underset{Z}{\overset{N-Y}{\|}}C \quad (III)$$

in which
Y and Z do not represent hydrogen, and
W represents O or S(O)$_g$, where g represents 0 or 2, and R$^8$ represents alkyl or benzyl,
optionally in the presence of a diluent and optionally in the presence of a base or a metal compound of the formula (IVa)

Me(V)$_2$      (IVa)

in which
Me represents a divalent transition metal atom and
V represents a chelate ligand, or that
(B) if K represents oxygen,
a compound of the formula (V)

$$\underset{Ar}{\overset{O}{\|}}C-\underset{X}{\overset{}{C}}H-Hal \quad (V)$$

in which
Hal represents halogen,
is reacted with a compound of the formula (VI)

$$\underset{S}{\overset{H\phantom{x}Y}{\underset{\|}{N}}}C\underset{Z}{} \quad (VI)$$

in which
Y and Z do not represent hydrogen,
optionally in the presence of a diluent to give a compound of the formula (VII)

$$\underset{Ar}{\overset{O}{\|}}C-\underset{X}{\overset{}{C}}H_2-\overset{H}{\underset{S}{\overset{\oplus}{N}}}\underset{Z}{\overset{Y}{}} \quad Hal^{\ominus} \quad (VII)$$

in which
which is reacted further, optionally in the presence of a base and optionally in the presence of a trivalent phosphorus compound, with elimination of sulphur and hydrogen halide, to give a compound of the formula (I) or that (C) a compound of the formula (II)

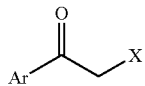
(II)

is initially condensed with a compound of the formula (VIII)

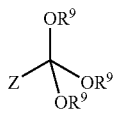
(VIII)

in which
$R^9$ represents $C_1$–$C_4$-alkyl,
and the resulting intermediate is reacted with an amine of the formula (IX)

Y—NH$_2$ (IX)

optionally in the presence of a diluent and optionally in the presence of a base, or that (D) if K represents sulphur,
a compound of the formula (I)

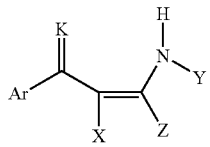
(I)

in which
K represents oxygen,
is reacted in the presence of a sulphurizing agent in the presence of a solvent, or that (E) if Ar represents Ar$^2$,
a compound of the formula (I$^1$)

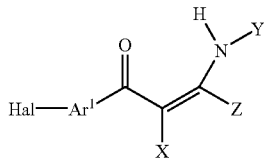
(I$^1$)

in which
Hal represents halogen,
is reacted with a boronic acid of the formula (X)

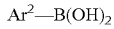
Ar$^2$—B(OH)$_2$ in the presence of a solvent, optionally in the presence of a base and/or a palladium metal complex.

2. A herbicidal, acaricidal and/or insecticidal composition comprising a compound of formula (I)

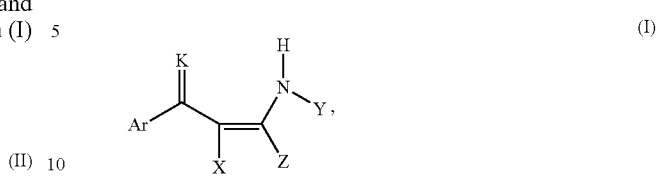
(I)

wherein
K represents oxygen or sulphur,
Ar represents Ar$^1$, where Ar$^1$ represents phenyl which is mono- to trisubstituted by fluorine, chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, trifluoromethyl, difluoromethoxy, trifluoromethoxy, methylenedioxy, tetrafluoroethylenedioxy, difluoromethylthio, trifluoromethylthio, trifluoromethylsulphinyl, trifluoromethylsulphonyl, benzyloxy, hydroxyl, mercapto, cyano or amino,
or represents Ar$^2$, where Ar$^2$ represents Ar$^1$ which is additionally substituted by phenyl or phenoxy, where these substituents are for their part mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano,
X represents —CN, —CO—NH$_2$, or

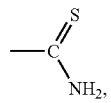

Y represents hydrogen, in each case optionally mono- or poly-hydroxy-substituted $C_1$–$C_6$-alkyl, $C_1$–$C_4$-halogenoalkyl, $C_3$–$C_6$-alkenyl, $C_3$–$C_6$-alkinyl, $C_1$–$C_4$-alkoxy-$C_2$–$C_3$-alkyl, di-$C_1$–$C_2$-alkoxy-$C_2$–$C_4$-alkyl, $C_1$–$C_2$-alkoxy-$C_2$–$C_4$-cyanoalkyl, $C_1$–$C_2$-alkylthio-$C_2$–$C_3$-alkyl, $C_1$–$C_5$-halogenoalkenyl or $C_1$–$C_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro,
Z represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro; and
one or more extenders and/or surfactants.

3. A method for controlling undesirable vegetation or animal pests, comprising allowing a compound according to formula (I) to act on one or more undesirable plants or animal pests and/or their habitat, wherein formula (I) comprises:

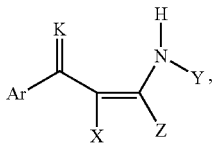

(I)

wherein

K represents oxygen or sulphur,

Ar represents $Ar^1$, where $Ar^1$ represents phenyl which is mono- to trisubstituted by chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, trifluoromethyl, difluoromethoxy, trifluoromethoxy, methylenedioxy, tetrafluoroethylenedroxy, difluoromethylthio, trifluoromethylthio, trifluoromethylsulphinyl, trifluoromethylsulphonyl, benzyloxy, hydroxyl, mercapto, cyano or amino, or represents $Ar^2$, where $Ar^2$ represents $Ar^1$ which is additionally substituted by phenyl, thienyl, tetrazolyl, triazolyl or phenoxy, where these substituents are for their part mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, X represents —CN, —CO—$NH_2$, or

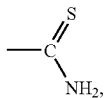

Y represents hydrogen, in each case optionally mono- or poly-hydroxy-substituted $C_1$–$C_6$-alkyl, $C_1$–$C_4$-halogenoalkyl, $C_3$–$C_6$-alkenyl, $C_3$–$C_6$-alkinyl, $C_1$–$C_4$-alkoxy-$C_2$–$C_3$-alkyl, di-$C_1$–$C_2$-alkoxy-$C_2$–$C_4$-alkyl, $C_1$–$C_2$-alkoxy-$C_2$–$C_4$-cyanoalkyl, $C_1$–$C_2$-alkylthio-$C_2$–$C_3$-alkyl, $C_1$–$C_5$-halogenoalkenyl or $C_1$–$C_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro, Z represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro.

4. A process for preparing a herbicidal composition comprising mixing a compound according to formula (I) with one or more extenders and/or surfactants, wherein formula (I) comprises:

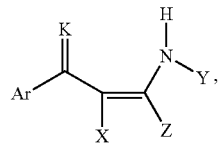

(I)

wherein

K represents oxygen or sulphur,

Ar represents $Ar^1$, where $Ar^1$ represents phenyl which is mono- to trisubstituted by chlorine, bromine, methyl, ethyl, propyl, i-propyl, s-, n-, i- or t-butyl, methoxy, ethoxy, propoxy, i-propoxy, s-, n-, i- or t-butoxy, allyloxy, methallyloxy, 2-butenyloxy, propargyloxy, 2-butinyloxy, trifluoromethyl, difluoromethoxy, trifluoromethoxy, methylenedioxy, tetrafluoroethylenedioxy, difluoromethylthio, trifluoromethylthio, trifluoromethylsulphinyl, trifluoromethylsulphonyl, benzyloxy, hydroxyl, mercapto, cyano or amino, or represents $Ar^2$, where $Ar^2$ represents $Ar^1$ which is additionally substituted by phenyl or phenoxy, where these substituents are for their part mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, X represents —CN, —CO—$NH_2$, or

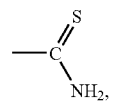

Y represents hydrogen, in each case optionally mono- or poly-hydroxy-substituted $C_1$–$C_6$-alkyl, $C_1$–$C_4$-halogenoalkyl, $C_3$–$C_6$-alkenyl, $C_3$–$C_6$-alkinyl, $C_1$–$C_4$-alkoxy-$C_2$–$C_3$-alkyl, di-$C_1$–$C_2$-alkoxy-$C_2$–$C_4$-alkyl, $C_1$–$C_2$-alkoxy-$C_2$–$C_4$-cyanoalkyl, $C_1$–$C_2$-alkylthio-$C_2$–$C_3$-alkyl, $C_1$–$C_5$-halogenoalkenyl or $C_1$–$C_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro, Z represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro.

5. A method for controlling undesirable vegetation or animal pests, comprising allowing a compound according to formula (I) to act on one or more undesirable plants or animal pests and/or their habitat, wherein formula (I) comprises:

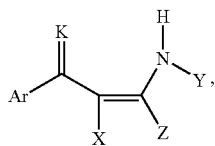

(I)

wherein

K represents oxygen or sulphur,

Ar represents Ar$^1$, where Ar$^1$ represents phenyl which is mono- to trisubstituted by fluorine, chlorine, bromine, methyl, ethyl, propyl, i-propyl, s-, n-, i- or t-butyl, methoxy, ethoxy, propoxy, -propoxy, s-, n-, i- or t-butoxy, allyloxy, methallyloxy, 2-butenyloxy, propargyloxy, 2-butinyloxy, trifluoromethyl, difluoromethoxy, trifluoromethoxy, methylenedioxy, tetrafluoroethylenedioxy, difluoromethylthio, trifluoromethylthio, trifluoromethylsulphinyl, trifluoromethylsulphonyl, benzyloxy, hydroxyl, mercapto, cyano or amino, or represents Ar$^2$, where Ar$^2$ represents Ar$^1$ which is additionally substituted by phenyl, pyridyl, thienyl, tetrazolyl, triazolyl or phenoxy, where these substituents are for their part mono- or disubstituted by fluorine, chlorine, bromine, methyl, ethyl, n- or i-propyl, s-, n-, i- or t-butyl, methoxy, ethoxy, i-propoxy, s-, n- or t-butoxy, trifluoromethyl, trifluoromethoxy, nitro or cyano, X represents —CN, —CO—NH$_2$, or

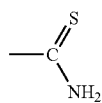

Y represents hydrogen, in each case optionally mono- or poly-hydroxy-substituted $C_1$–$C_6$-alkyl, $C_1$–$C_4$-halogenoalkyl, $C_3$–$C_6$-alkenyl, $C_3$–$C_6$-alkinyl, $C_1$–$C_4$-alkoxy-$C_2$–$C_3$-alkyl, di-$C_1$–$C_2$-alkoxy-$C_2$–$C_4$-alkyl, $C_1$–$C_2$-alkoxy-$C_2$–$C_4$-cyanoalkyl, $C_1$–$C_2$-alkylthio-$C_2$–$C_3$-alkyl, $C_1$–$C_5$-halogenoalkenyl or $C_1$–$C_6$-cyanoalkyl, represents in each case optionally methyl-, methoxy-, ethoxy-, trifluoromethyl-, cyano-, chlorophenyl-, benzyl-, hydroxymethyl-, fluorine- or chlorine-substituted $C_3$–$C_6$-cycloalkyl or $C_3$–$C_6$-cycloalkyl-$C_1$–$C_2$-alkyl in which optionally one methylene group may be replaced by oxygen or sulphur, represents benzyl, phenethyl or pyridylmethyl, each of which is optionally mono- to trisubstituted by fluorine, chlorine, bromine, methyl, methoxy, trifluoromethyl, difluoromethoxy, trifluoromethoxy, cyano or nitro, Z represents hydrogen, methyl, ethyl, represents phenyl or benzyl, each of which is optionally mono- or disubstituted by fluorine, chlorine, bromine, methyl, methoxy, trifluoromethyl, trifluoromethoxy, cyano or nitro; and one or more extenders and/or surfactants.

\* \* \* \* \*